United States Patent [19]
Huang et al.

[11] Patent Number: 5,922,876
[45] Date of Patent: Jul. 13, 1999

[54] PREPARATION OF OXYMORPHONE FROM MORPHINE

[75] Inventors: Bao-Shan Huang; Yansong Lu; Ben-Yi Ji, all of Edison, N.J.; Aris P Christodoulou, New York, N.Y.

[73] Assignee: Penick Corporation, Newark, N.J.

[21] Appl. No.: 09/116,284

[22] Filed: Jul. 16, 1998

Related U.S. Application Data

[62] Division of application No. 08/893,464, Jul. 11, 1997, Pat. No. 5,869,669
[60] Provisional application No. 60/022,685, Jul. 26, 1996, and provisional application No. 60/045,081, Apr. 29, 1997.
[51] Int. Cl.$^6$ ........................ C07D 489/08; C07D 489/02
[52] U.S. Cl. .............................................. 546/45; 546/44
[58] Field of Search .......................................... 546/45, 44

[56] References Cited

U.S. PATENT DOCUMENTS 5,112,975   5/1992   Wallace ...................................... 546/45

*Primary Examiner*—Alan L. Rotman
*Assistant Examiner*—Charanjit S. Aulakh
*Attorney, Agent, or Firm*—Burgess, Ryan & Wayne

[57] ABSTRACT

A process is provided for preparing oxymorphone from morphine by: (a) reacting morphine with an acyl halide or anhydride to form 3-acylmorphine, or (b) reacting morphine with benzyl-halide to form 3-benzylmorphine, and thereafter either by (3*a*) or (3*b*):

(3*a*) introducing a β-oriented hydroxy group at the 14-position of the 3-acyl- or 3-benzyl-morphinone with aqueous hydrogen peroxide and an acid at at temperature of about 15° to about 70° C. to form the 3-acyl or 3-benzyl-14-hydroxymorphinone;

(3*b*) acylating the 3-acyl or 3-benzyl-morphinone with an acylating agent so as to form the dienol acylate followed by oxidizing the dienol acetate to the corresponding 3-acyl or 3-benzyl-14-hydroxymorphinone;

(4) hydrogenating the 3-acyl-14-hydroxymorphinone with a catalyst so as to form the 3-acyloxymorphone;

(5) hydrolyzing the 3-acyl-oxymorphone with aqueous acidic or basic solution to form oxymorphone;

(6) hydrogenating the 3-benzyl-14-hydroxymorphinone with a catalyst so as to form oxymorphone.

2 Claims, No Drawings

PREPARATION OF OXYMORPHONE FROM MORPHINE

RELATED APPLICATIONS

This application is a divisional application of Ser. No. 08/893,464 filed Jul. 11, 1997 now U.S. Pat. No. 5,869,669, which is hereby incorporated by reference and is based on provisional patent application Ser. No. 60/022,685, filed Jul. 26, 1996, and provisional patent application Ser. No. 60/045,081, filed Apr. 29, 1997.

BACKGROUND OF THE INVENTION

1). Field of the Invention

This invention relates in general to process for the conversion of normorphinone and its derivatives, which can be synthesized from morphine, to the corresponding 14-hydroxynormorphinone and its derivatives including oxycodone, oxymorphone, noroxymorphone, and naltrexone. Noroxymorphone is a key intermediate for the production of important narcotic analgesics and antagonists. In another aspect, the invention is directed to certain novel intermediates.

2). Background Art

14-Hydroxy-substituted morphine derivatives are important narcotic analgesics and/or antagonists. These drugs include oxycodone, oxymorphone, nalbuphine, naloxone, naltrexone, and nalmefene. They are readily synthesized from thebaine, which is a minor component of gum opium. As the supply of thebaine is limited and the demand is increasing, therefore, the price of thebaine is high. As a result, many alternative approaches have been made for the preparation of 14-hydroxymorphine derivatives.

The reported efforts for preparing these narcotics bearing a 14-hydroxy group from readily abundant starting materials morphine or codeine (a minor component of gum opium, which may also be synthesized by methylation of morphine) are summarized as the following: (1) the conversion of codeine to thebaine through dihydrocodeinone (5.4% yield, H. Rapoport, et al., J. Am. Chem. Soc., vol. 89, 1967, p. 1942 and H. Rapoport, et al., J. Org. Chem., vol. 15, 1950, p. 1103), codeinone (20% yield, I. Seki, Chem. Pharm. Bull., vol. 18, 1970, p. 671 and H. Rapoport, et al., J. Am. Chem. Soc., vol. 77, 1955, p. 490) or 6-methyl ether of codeine (using manganese dioxide, 67% yield, R. B. Barber, et al., J. Med. Chem., vol. 18, 1975, p. 1074); (2) the oxidation of codeinone pyrrolidinyl di-enamine to 14-hydroxycodeinone (30–40% yield, I. Seki, Chem. Pharm. Bull., vol. 18, 1970, p. 671); (3) the direct allylic oxidation of codeine to the corresponding 14-hydroxy derivatives with manganese dioxide (I. Brown, et al., J. Chem. Soc., 1960, p. 4139), and selenium dioxide plus t-butyl hydrogen peroxide (M. A. Schwartz, et al., J. Med. Chem., vol. 24, 1981, p. 1525); and (4) the six-step transformation of codeine to noroxycodone (52% yield) and noroxymorphone (43% yield) using photochemically generated singlet oxygen (M. A. Schwartz, et al., J. Med. Chem. vol. 24, 1981, p. 1525); and (5) the preparation of noroxymorphone from morphine through an intermediate with carbamate protection on the nitrogen atom (17-position) or a carbonate protecton at the 3 position and the carbamate protection at the 17 position of normorphinone dienol acetate with MCPBA in the substantial absence of water (37% yield, Wallace, U.S. Pat. No. 5,112,975). These processes suffer from either low yields, long steps, not amenable to scale-up, or involve the use of environmentally unfriendly heavy metals.

It is therefore an object of the present invention to provide methods for the conversion of normorphinone and its derivatives to the corresponding 14-hydroxynormorphinone and its derivatives. A further object of the invention is to provide processes which provide relatively high yields of the desired products. Another object is to provide methods which are environmentally safe and avoid the use of heavy metals.

Another object of the present invention is to provide processes which can use morphine or codeine as starting material instead of the scarce thebaine. Codeine is a component of gum opium and can also be produced by methylation of morphine using known prior art techniques. A still further object of the present invention is to provide the use of an aqueous system in the oxidation step to form 14-hydroxynormorphinone wherein Q and Q' are individually selected from hydrogen, lower alkyl, trifluoromethyl, nitro, dialkylamino, cyano;

preferably, R is methyl (when the desired products are oxycodone and oxymorphone), cyclopropylmethyl (when the desired products are naltrexone and nalmefene), cyclobutylmethyl (when the desired product is nalbuphine), and benzyl (when the desired products are naloxone, naltrexone, nalbuphine, or nalmefene);

R' is methyl, ethyl, 2-(4-morpholinyl)ethyl, benzyl, substituted-benzyl (as defined above), benzyloxycarbonyl or the group having the formula:

R"C(O)— 

wherein: R" is lower alkyl of 1–4 carbon atoms;

preferably, R' is methyl (when the desired product is oxycodone), benzyl (when the desired products are oxymorphone and 14-hydroxyl-normorphinones), or acyl (when the desired product is oxymorphone) and R" is methyl;

from the corresponding normorphinones having the formula:

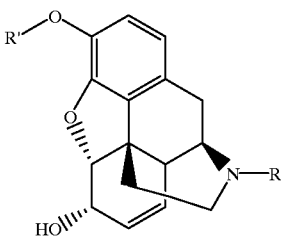

wherein R and R' are as defined above;

by reacting the normorphinones (as defined above) either (1) or (2) of the following processes:
(1) directly with an oxidizing agent, hydrogen peroxide, at a temperature of about 15° C. to about 70° C., preferably 40° C. to 50° C., in the presence of an acid such as formic which is not only environmentally friendly, but also desirable in which to conduct the subsequent hydrogenation reaction without the need for isolating the 14-hydroxynormorphinone intermediate. A still further object is to provide certain intermediates which are novel compositions. It is a further object of this invention to provide intermediates for specific products, such as oxycodone, oxymorphone, naltrexone and noroxymorphone. These and other objects will readily become apparent to those skilled in the art in light of the teachings herein disclosed.

SUMMARY OF THE INVENTION

In its broad aspect, the present invention pertains to processes for the preparation of 14-hydroxy-normorphinones of the formula:

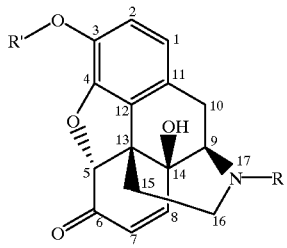

and certain derivatives thereof as hereinafter indicated. In the formula above R is selected from the group consisting of lower alkyl of 1–7 carbon atoms, cycloalkylalkyl with 3–6 ring carbon-atoms benzyl and substituted-benzyl having the formula:

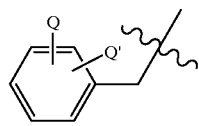

acid, tartaric acid, acetic acid, or other mineral acids, preferably formic acid; in a suitable non-reactive solvent such as water, acetic acid, THF, DMSO or a mixture of solvents such as ETOAc/H$_2$O suitable for solubilizing or suspending the reactants, preferably water, for a period of 1 to 24 hours, which depends on the scale of the reaction; or (2) in a two-step manner by first with an acyl halide having the formula:

R"C(O)X wherein: R" is defined above, preferably methyl;

X is Cl or Br, preferably Cl;

or an acid anhydride having the formula:

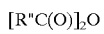
[R"C(O)]$_2$O wherein R" is as defined above;

and the corresponding acid salt having the formula:

R"COOM wherein: R" is as defined above,

M is sodium or potassium atom, preferably sodium atom;

with or without a cosolvent such as toluene, DMF, or DMAC, preferably toluene; heating at a temperature of about 60° C. to about 150° C., preferably 110° C. for 1 to 24 hours, depending on the scale of the batch, to produce the dienol acylate having the formula:

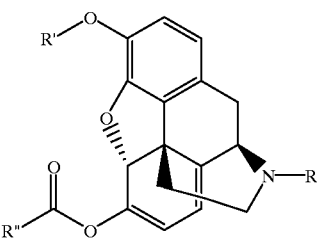

wherein: R, R', and R" are defined as above; then followed by reacting the dienol acylate with either an oxidizing agent under the conditions described in (1) or reacting with a peroxyacid such as 3-chloroperoxybenzoic acid (MCPBA) in a weak acid such as acetic acid or formic acid, with or without water and with or without a cosolvent, to help dissolve the peroxyacid and the reactant.

DESCRIPTION OF THE PREFERRED EMBODIMENTS

The embodiments of the present invention will be discussed with reference to various examples of reactions via which the 3(O)-substituted- and/or 17(N)-substituted-14-hydroxynormorphinone can be prepared. The R, R' and R" are as previously defined above.

Key features of the novel reactions of the invention are made possible by the combination of several essential novel concepts and techniques, and reside in (a) the conversion of the 17(N),3(O)-substituted normorphinone having the formula:

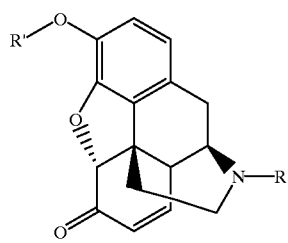

to the corresponding 14-hydroxy-17(N),3(O)-substituted-normorphinone having the formula:

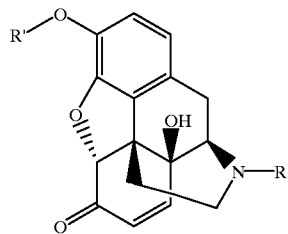

with hydrogen peroxide in an aqueous system in the presence of an acid;

(b) the conversion of the 17(N),3(O)-substituted-normorphinone dienol acylate having the formula:

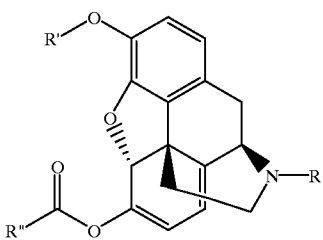

to the corresponding 14-hydroxy-17(N),3(O)-substituted-normorphinone having the formula:

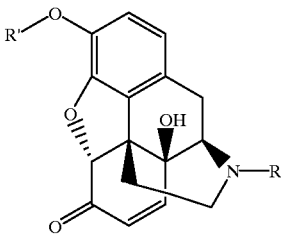

with an oxidizing agent chosen from aqueous hydrogen peroxide or a peroxycarboxylic acid in an aqueous system in the presence of a weak organic acid;

(c) the oxidation reaction to form 14-hydroxy-17(N),3(O)-substituted-normorphinone having the formula:

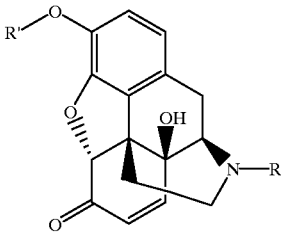

in an acetic aqueous system, which is very desirable for the following catalytic hydrogenation step;

(d) the 14-hydroxy 3(O)-substituted and/or 17(N)-substituted-normorphinone having the formula:

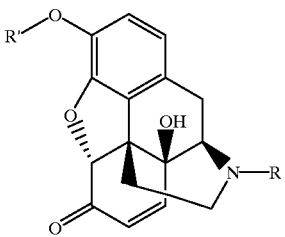

may further react in specific ways to form oxycodone, oxymorphone, naltrexone, and noroxymorphone. The later is a common intermediate for naloxone, naltrexone, nalmefene, and nalbuphine;

(e) the choice of a preferred substitution group depends on the kind of desired product in such a way to facility the ease of operation, solvent and reagent consumption.

The advantages of the method of the invention for the preparation of oxycodone include, among others:

(a) the use of a currently abundant starting material, codeine, which is a minor component of gum opium and can also be produced by methylation of morphine using prior art techniques. This method does not need to demethylate the N-methyl group on the 17 position of codeine, protect the 17-nitrogen of norcodeine and norcodeinone with a carbamate and then deprotect the 14-hydroxy-N-ethoxycarbonylnorcodeinone, finally, remethylate the same nitrogen as disclosed in U.S. Pat. Nos. 4,472,253, 4,639,520 and 4,795,813;

(b) the use of an aqueous system in the oxidation of normorphinones or normorphinone dienol acyletes is not only environmentally friendly but also desirable for the following hydrogenation reaction, since there is no need to isolate the intermediate 14-hydroxycodeinone. The basic nitrogen on the 17-position is protonated in the acidic aqueous system. This greatly contributes to the high solubility of the reactant and the product.

This novel synthesis route affords high yields, good reliability, and straightforward operation and control at each and every step of the synthesis and a major reduction in the cost of the synthesis of oxycodone, oxymorphone, noroxymorphone, naltrexone and nalbuphine.

Thus, for the synthesis of oxycodone from codeine in this invention, the starting material, which has the formula:

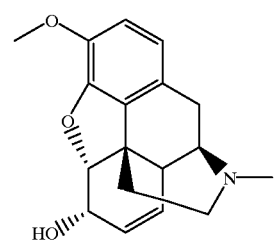

is converted to codeinone having the formula:

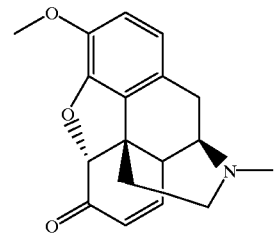

by the prior art method such as Swern oxidation (DMSO/acid halide or acid anhydride).

In the first method of this invention, codeinone is reacted with hydrogen peroxide in water in the presence of an acid at about 15° to about 70° C. for a period of time depending on the scale of the reaction to afford 14-hydroxycodeinone in good yield. 14-Hydroxycodeinone so produced is hydrogenated in the same reaction media with a catalyst to afford oxycodone in good yield. Preferably the temperature is between about 40° to about 50° C. and the acid is formic acid.

The sequence of steps in the first method for the synthesis of oxycodone from morphine or codeine can be illustrated as follows:

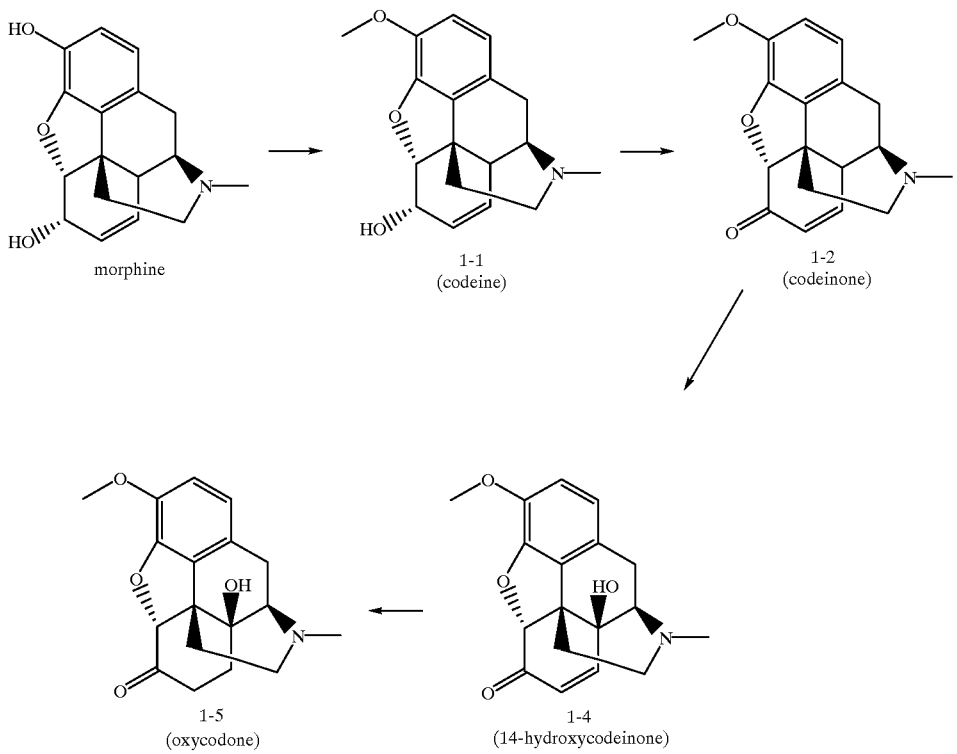

In this and the reaction sequences which are hereinafter shown, the hyphenated two digit descriptor appearing beneath each formula corrsponds to the same discriptor appearing after the title to the Examples. Accordingly, the solvents, reactants, temperatures, times and yield are set forth in the examples for each step of the overall reaction.

In the present invention it was observed that the yields of the intermediate products were markedly increased by first acylating the normorphinones to the corresponding dienol acylates and then oxidizing the acrylates to the corresponding 14-hydroxynormorphinones as opposed to the direct oxidation of normorphinones to the corresponding 14-hydroxynormorphinones. Although this involves an extra step, the overall yield is higher. For example, the oxidation of codeinone dienol acetate to 14-hydroxycodeinone provided a yield of 70 to 80% after chromatography whereas direct oxidation of codeinone to the 14-hydroxycodeinone gives about 40% yield.

Accordingly, in a second method of this invention, codeinone is first converted to codeinone dienol acetate by prior art methods (DE 902257, 1957 and I. Brown, JCS, 1960, p. 4139) and then the codeinone dienol acetate is reacted with hydrogen peroxide under the conditions set forth in the first process to 14-hydroxycodeinone which is hydrogenated to oxycodone in excellent yields. Alternatively, codeinone dienol acetate is reacted with a peroxyacid oxidizing agent in an aqueous or non-aqueous system with a weak acid at room temperature to form 14-hydroxycodeinone in excellent yield. Again the product, 14-hydroxycodeinone, in its reaction mixture is suitable for the next reaction, the catalytic hydrogenation, without isolation of the 14-hydroxycodeinone by adding the catalyst and hydrogenating the mixture and then isolating oxycodone. Preferably the peroxyacid oxidizing agent is 3-chloroperbenzoic acid, perbenzoic acid, peroxyacetic acid; more preferably 3-chloroperbenzoic acid. A non-reactive cosolvent such as ethyl acetate, tetrahydrofuran, dioxane, is used to dissolve the oxidizing agent. The preferred weak acid is acetic acid or formic acid, which also serves as the solvent. Conducting the reaction with or without water or oxalic acid does not change the yield.

The sequence of steps for the second method wherein codeinone is converted to codeinone dienol acetate in the synthesis of oxycodone from morphine can be illustrated as follows:

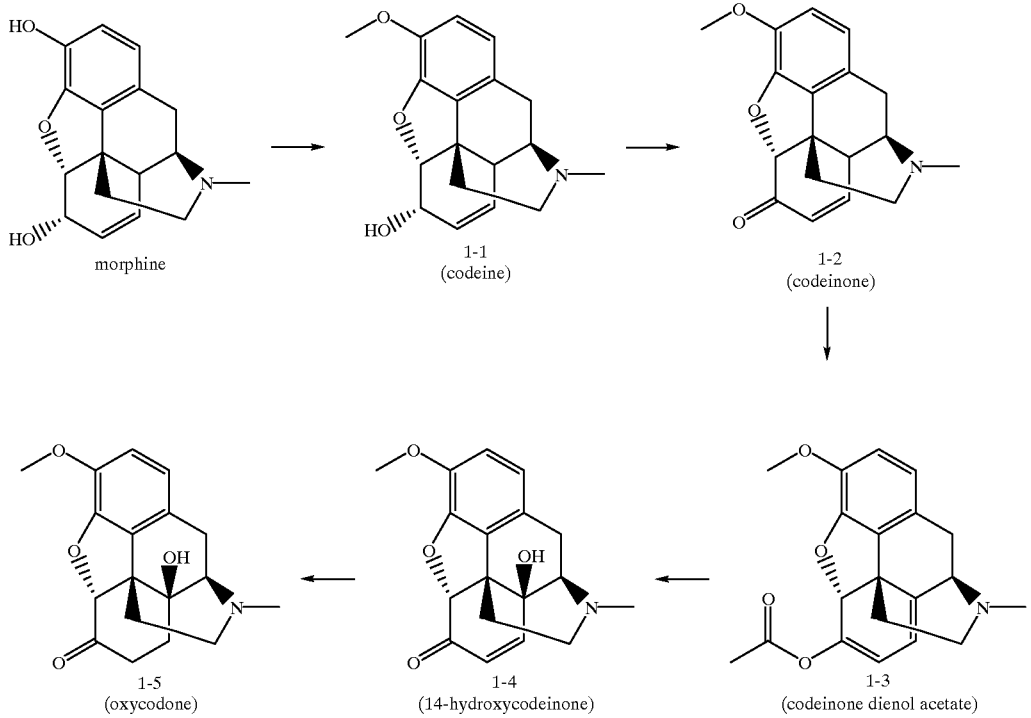

For the synthesis of oxymorphone from morphine in the present invention, (a) the first step is to protect the phenolic hydroxy on the 3-position of morphine to form the 3(O)-protected-morphine having the formula:

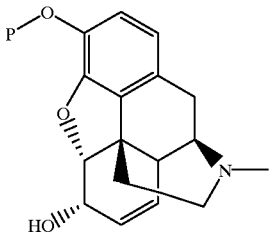

wherein P=$P_1$ or $R_2$. P is a suitable protecting group which is stable under the reaction conditions and easily removable by mild hydrolysis with an acid or base (for $P_1$) or under catalytic hydrogenation (for $P_2$). $P_1$ includes acyl, benzoyl and alkoxycarbonyl. $P_2$ includes benzyl, substituted benzyl and benzyloxycarbonyl.

(b) the second step is to oxidize the 3(O)-protected morphine to 3(O)-protected-morphinone having the formula:

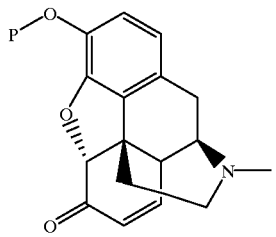

by any of the prior art methods such as Swern oxidation (DMSO/acid halide or acid unhydrite).

(c) the third step is to convert the 3(O)-protected-morphinone to the 14-hydroxy-3-(O)-protected-morphinone using the techniques disclosed in this invention as set forth in the conversion of codeinone to 14-hydroxycodeinone in the synthesis of oxycodone. The intermediate, 3(O)-protected-codeinone dienol acylate, is a novel compound having the formula:

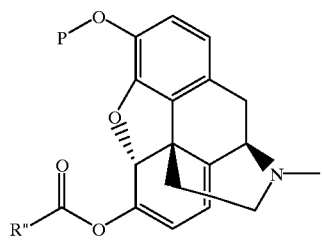

wherein P and R" are as defined above; preferably $P_1$ is acetyl and $P_2$ is benzyl.

(d) depending on the particular protection group, $P_1$ or $P_2$, the fourth step is either (i) to first produce the 7,8-double bond of 3-(O)-$P_1$-protected morphinone and then to remove the protection group by acid or base hydrolysis to produce oxymorphone or (ii) to hydrogenate the 7,8-double bond and deprotect simultaneously the 3-(O)-$P_2$-protected morphinone to oxymorphone.

This synthesis of oxymorphone from morphine wherein $P_1$ is acetyl can be illustrated below:

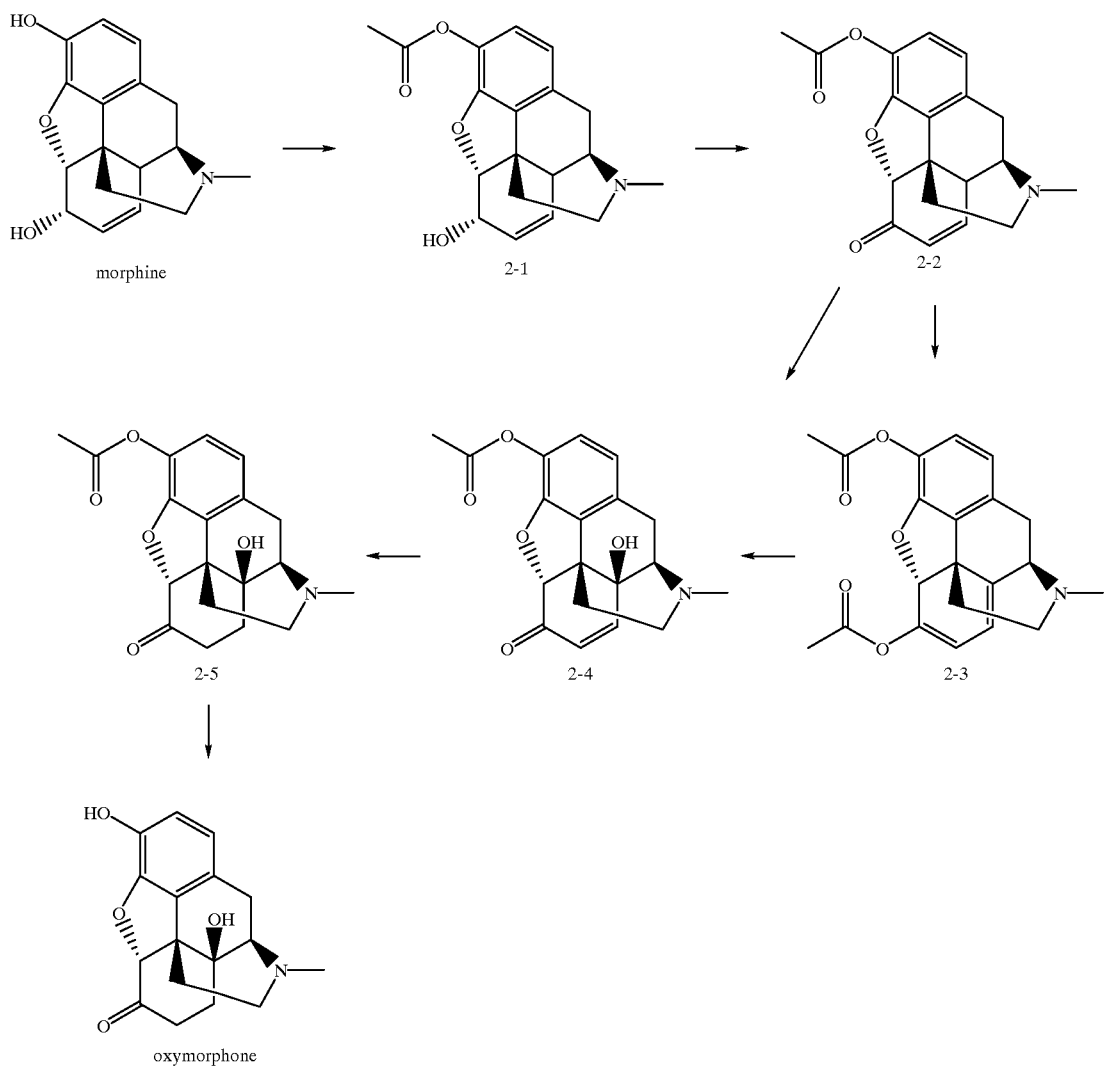

wherein the hyphenated two digits below each formula identifies this corresponding examples as previously indicated.

The synthesis of oxymorphone from morphine wherein $P_2$ is benzyl can be shown as follows:

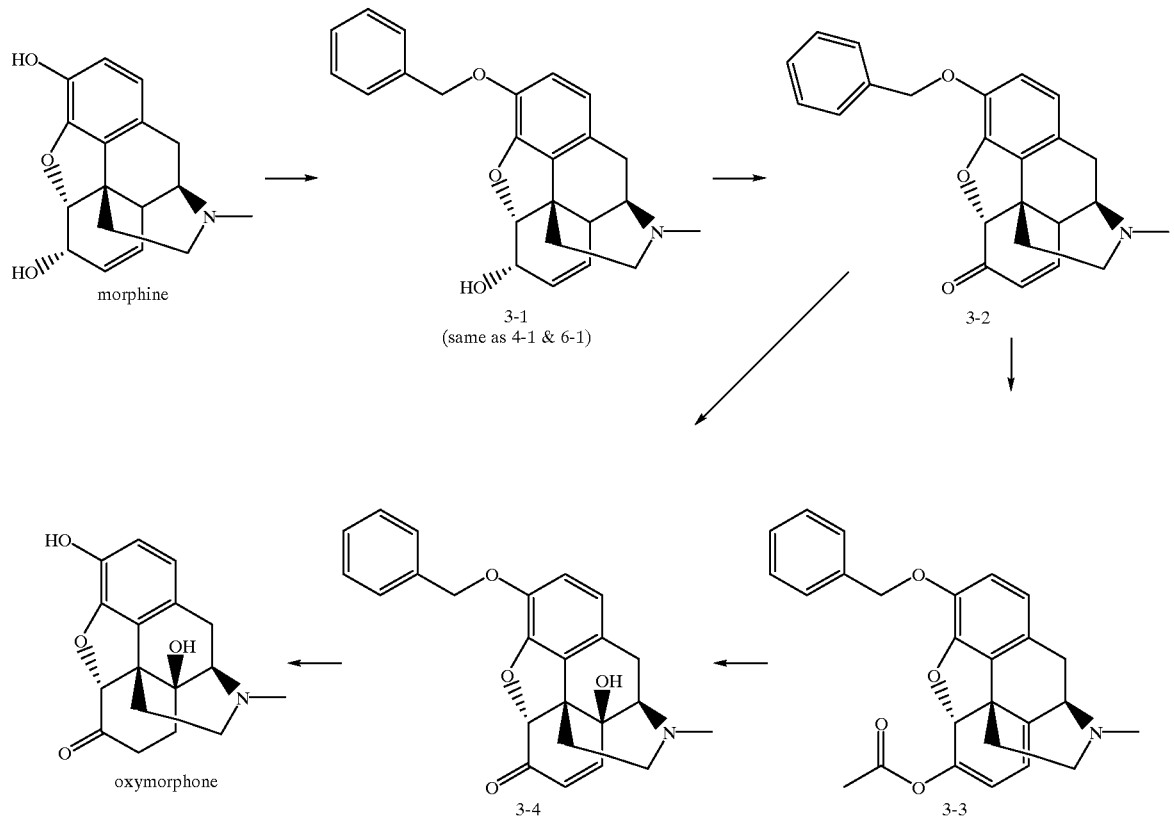

For the synthesis of noroxymorphone from morphine in another embodiment of this invention, morphine is converted to 3-benzylmorphine, which is acetylated to 6-acetyl-3-benzlmorphine having the formula:

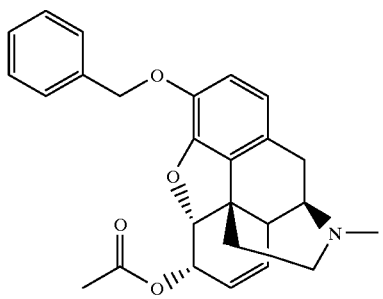

6-acetyl-3-benzylmorphine is N-de-methylated with 1-chloroethyl chloroformate or cyanogen bromide and followed by acid hydrolysis to 3-benzylnormorphine.

3-Benzylnormorphine is reacted with benzyl halide in the presence of a base such as sodium or potassium bicarbonate to produce 3,17-dibenzylnormorphine, a novel compound, which is oxidized to 3,17-dibenzylnormorphinone, a novel compound, by Swern oxidation. Using the conditions set forth in this invention, 3,17-dibenzylnormorphinone is oxidized to 3,17-dibenzyl-14-hydroxynormorphinone either by directly reacting with hydrogen peroxide in formic acid or by first converting to 3,17-dibenzylnormorphinone dienol acylate, a novel compound, and then reacting the latter with hydrogen peroxide in formic acid or a peroxyacid as set forth in the synthesis of oxycodone. Without isolation of 3,17-dibenzyl-14-hydroxynormorphinone from its reaction mixture it is hydrogenated to remove the two benzyl groups and reduce the 7,8-double bond simultaneously to produce noroxymorphone in good yields.

The synthesis of noroxymorphone from morphine can be illustrated as follows:

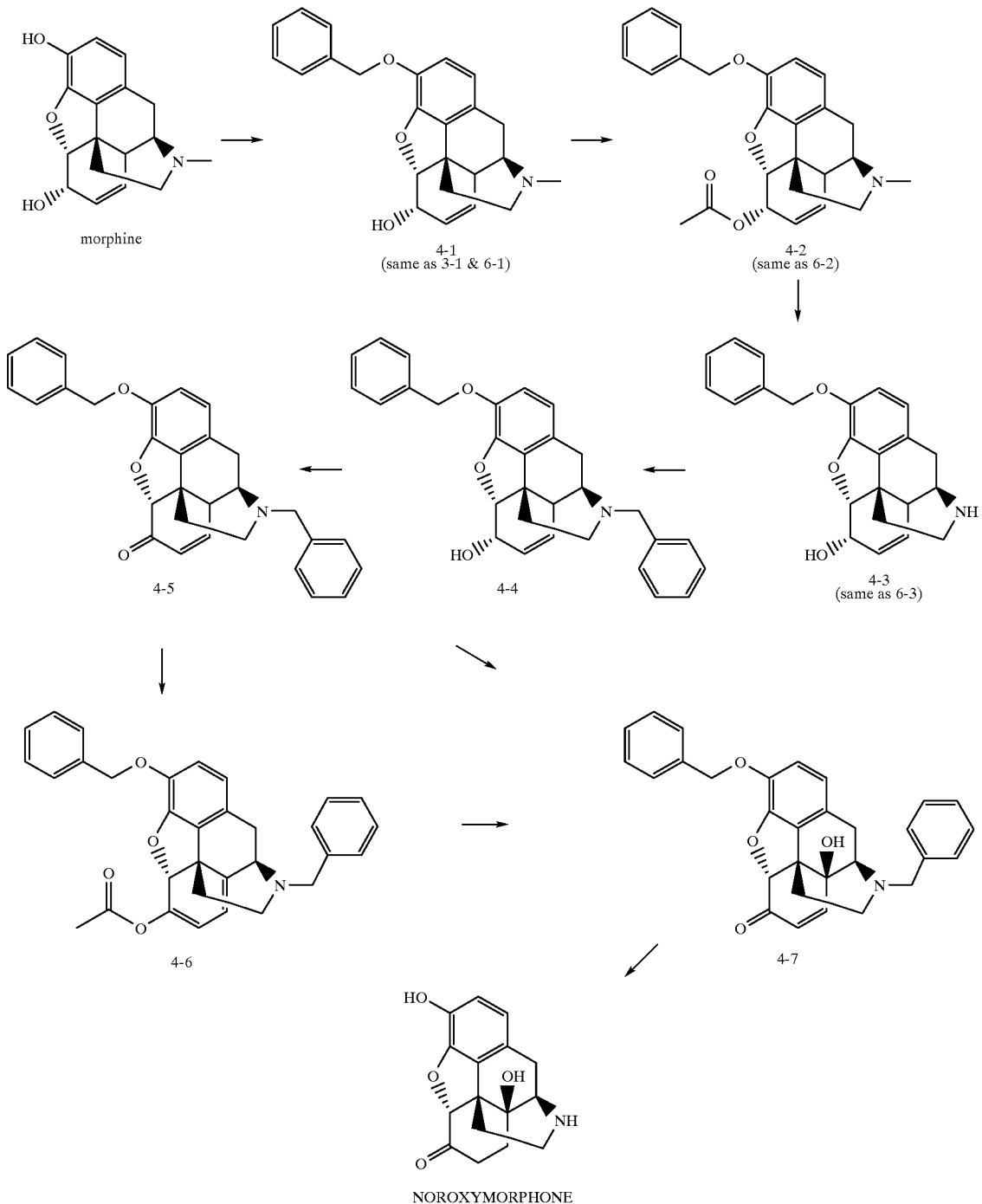

For the synthesis of 3-methylnaltrexone from codeine in this invention, codeine is converted to 6-acetylcodeine, which is N-demethylated to 6-acetylnorcodeine hydrochloride, followed by alkylating the nitrogen to form 17-cyclopropylmethylnorcodeine. The latter is oxidized to 17-cyclopropylmethylnorcodeinone. As set forth in the synthesis of oxycodone in this invention, 17-cyclopropylmethylnorcodeinone is converted to 14-hydroxy-17-cyclopropylmethyinorcordeinone either by oxidizing with hydrogen peroxide in formic acid; or by first converting to 17-cyclopropylmethylnorcordeinone dienol acetate, a novel compound, then oxidizing with either hydrogen peroxide or MCPBA. 14-Hydroxy-17-cyclopropyimethylnorcodeinone is hydrogenated to 3-methyinaltrexone. 3-Methylnaltrexone can be demethylated to naltrexone with $BBr_3$, a prior art method. The reaction can be illustrated as follows:

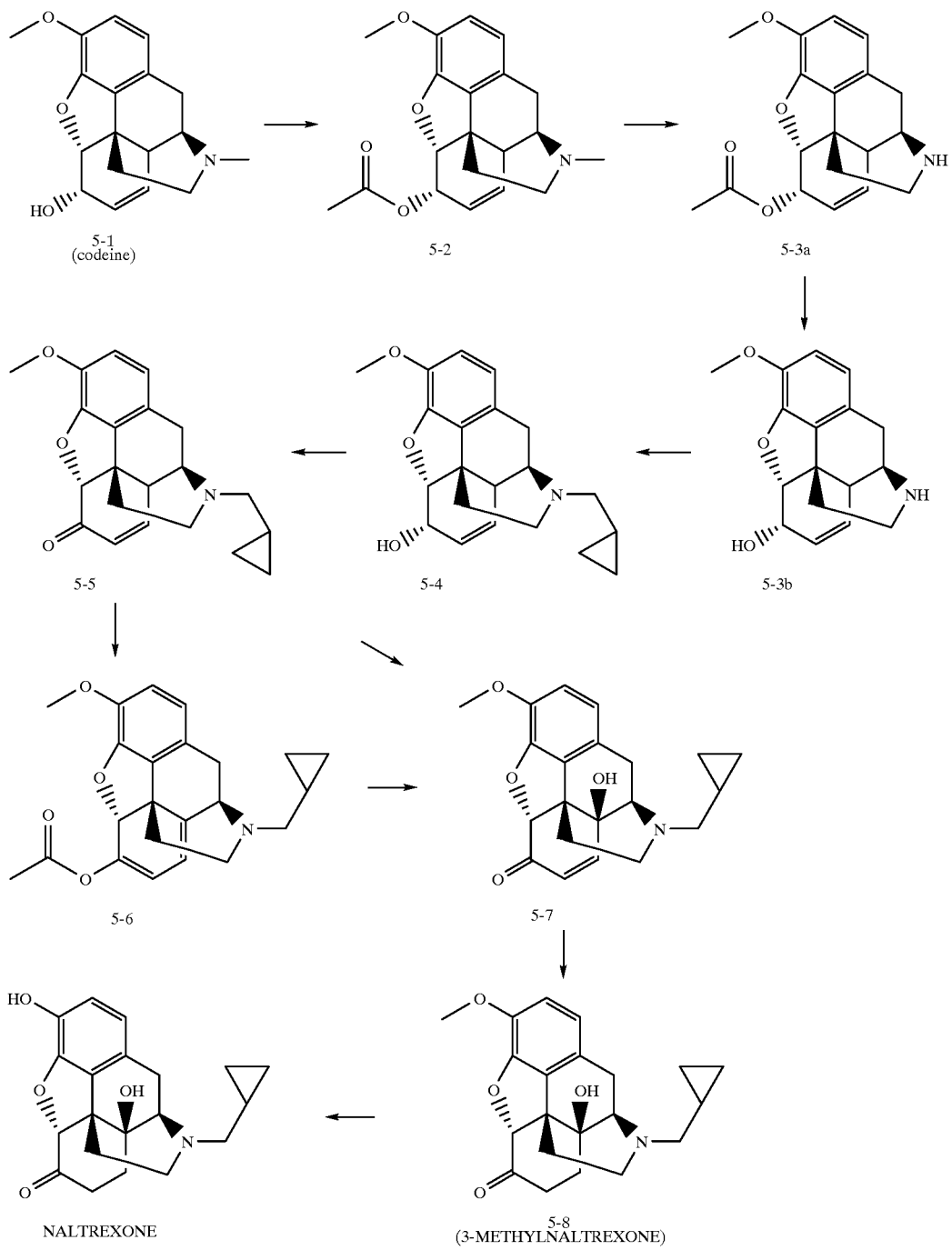

For the synthesis of naltrexone from morphine in this invention, morphine is converted to 3-benzylnormorphine as described above in the synthesis of noroxymorphone. 3-Benzylnormorphine is reacted with cyclopropylmethyl halide to produce 3-benzyl-17-cyclopropylmethylnormorphine, a novel compound, which is oxidized to 3-benzyl-17cyclopropylmethyl-normorphinone, a novel compound, by Swern oxidation. Using the conditions set forth in this invention, 3-benzyl-17-cyclopropylmethylnormorphinone is oxidized to 3-benzyl-17-cyclopropylmethyl-14-hydroxynormorphinone either by directly reacting with hydrogen peroxide in formic acid or by first converting to 3-benzyl-17-cyclopropylmethylnormorphinone dienol acylate, a novel compound, and then reacting the latter with hydrogen peroxide in formic acid or a peroxyacid as set forth in the synthesis of oxycodone. Without isolation of 3-benzyl-17-cyclopropylmethyl-14-hydroxynormorphinone from its reaction mixture, it is hydrogenated to remove the benzyl group and reduce the 7, 8-double bond simultaneously to provide naltrexone in good yield.

This synthesis of Naltrexone from morphine is shown below:

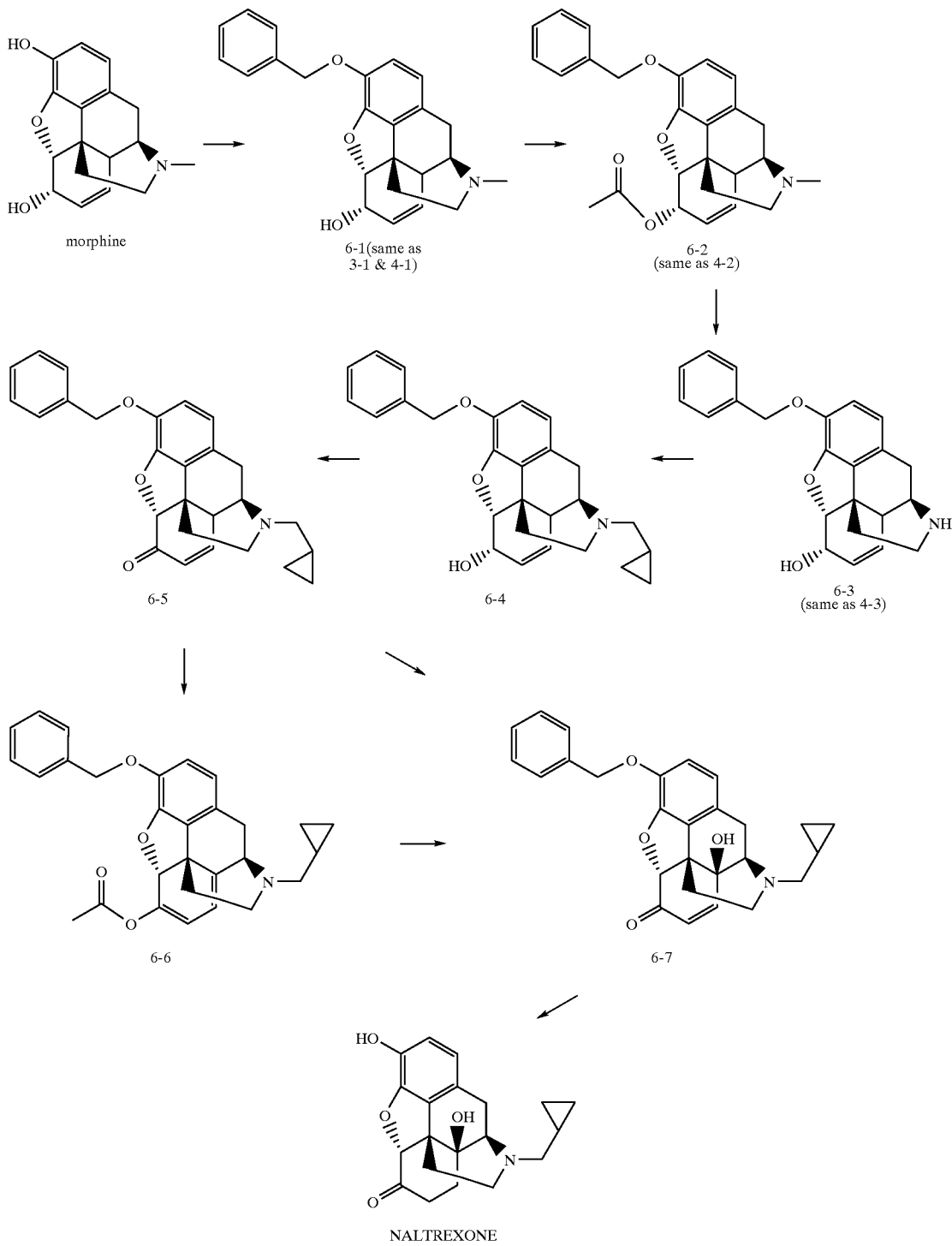
A general scheme for the synthesis of noroxymorphone from morphine can be depicted below wherein P, Q, Q' and R" are as previously indicated.

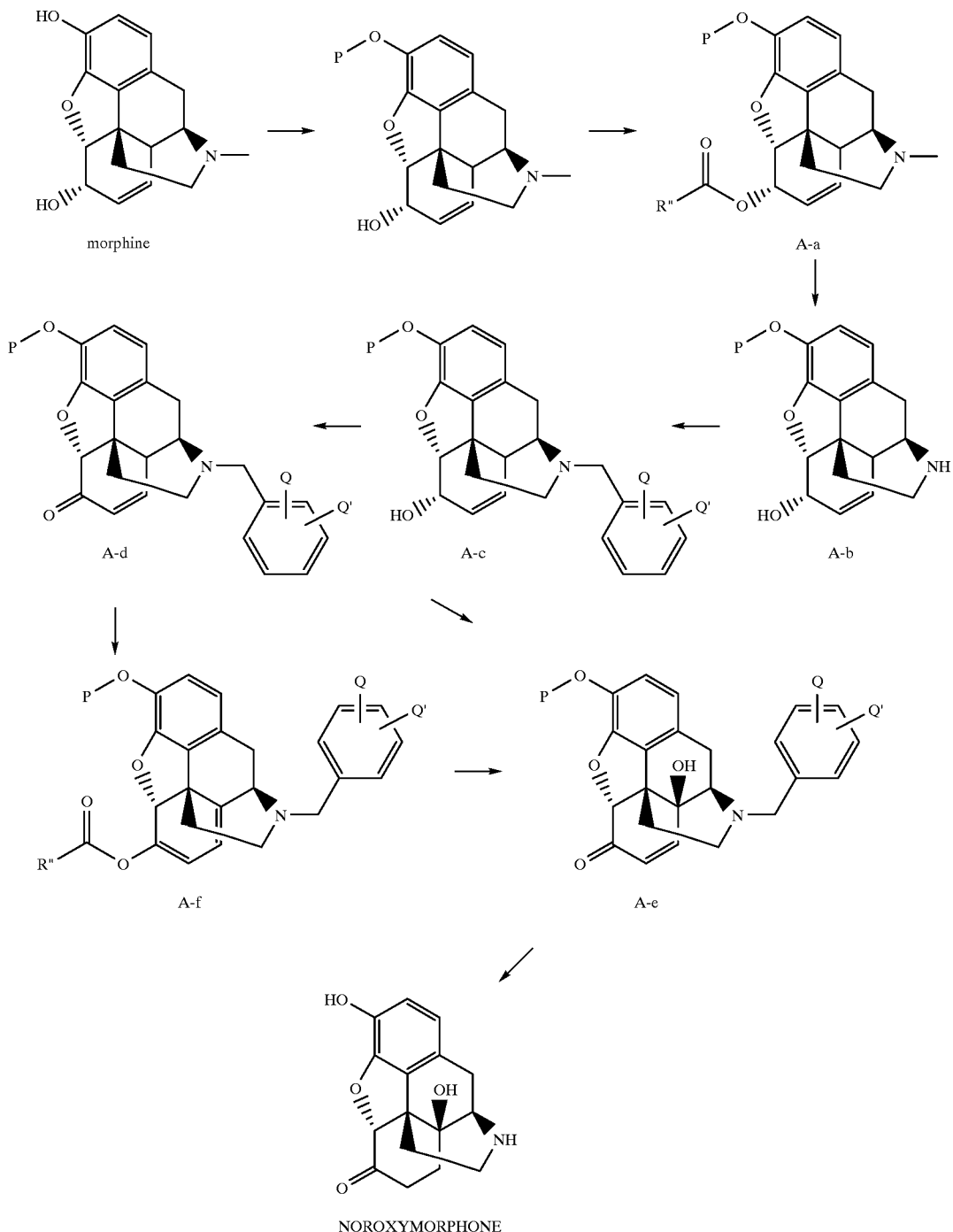

As hereinbefore indicated, certain intermediate compounds found during the synthesis of the desired end products, are themselves novel compositions of matter. These compounds are set forth in the claims.

The following examples are illustrative of the invention.

A. Synthesis of Oxycodone From Codeine Through Codeinone Dienol Acetate

EXAMPLE 1

Preparation of codeinone (1-2)

To a solution of dimethylsulfoxide (16.53 g, 0.21 mole) in $CH_2Cl_2$ (80 ml) at −78° C. was added dropwise a solution of oxalyl chloride (13.01 g, 0.10 mole) in $CH_2Cl_2$ (50 ml) over a period of 40 min. After stirring for 10 min., a solution of codeine (20.33 g, 0.068 mole) in $CH_2Cl_2$ (100 ml) was added over 50 min. while keeping the reaction mixture at −78°C. After stirring at −78° C. for 2 hr., $Et_3N$ (50 ml) was added, followed by $CH_2Cl_2$ (100 ml). The reaction mixture was allowed to warm-up to room temperature, washed with water (6×150 ml), dried over anhydrous $Na_2SO_4$ and evaporated to dryness in vacuo to give codeinone (25.57 g). IR (KBr)(v, $cm^{-1}$): 1668 (s, sharp, —C=C—C=O); NMR ($\delta$H)($CDCl_3$): 6.67 (1, d, J, 8.2, 2-H), 6.62 (1, d, J, 10.2, 8-H), 6.59 (1, d, J, 8.2, 1-H), 6.07 (1, dd, J, 10.2 & 2.9, 7-H), 4.68 (1, s, 5-H), 3.85 (3, s, OCH$_3$), 3.45–3.35 (1, m, 9-H), 3.25–3.17 (1, m, 14-H), 3.10 (1, d, J, 18.5, 10-H$_\beta$), 2.61 (1, dm, J, 11.9, 16-H$_e$), 2.45 (3, s, NCH$_3$), 2.30 (1, dd, J, 18.5 & 5.5, 10-H$_\alpha$), 2.30 (1, td, J, 11.9 & 3.7, 16-H$_a$), 2.06 (1, td, J, 12.0 & 4.8, 15-H$_a$), 1.85 (1, dm, J, 12.5, 15-H$_e$).

EXAMPLE 2
Preparation of codeinone dienol acetate (1-3)

A mixture of codeinone (5.98 g, 0.02 mole), sodium acetate (1.77 g, 0.02 mole) and acetic anhydride (35.76 g, 0.35 mole) in toluene (6 ml) was heated at 90–105° C. for 5 hr, cooled, diluted with CH$_2$Cl$_2$ (300 ml), and basified with NaHCO$_3$ (66 g in 300 ml of ice-cold water). The organic portion was separated, washed with water (4×150 ml), dried over anhydrous Na$_2$SO$_4$, and evaporated to dryness in vacuo to give an oil (9.4 g), which was chromatographed on silica gel with 5% CH$_3$OH in CH$_2$Cl$_2$ to give codeinone dienol acetate as brown needles (5.62 g, 83% yield), IR (KBr)(v, cm$^{-1}$): 1745 (s, sharp, C=C—OAc); NMR ($\delta_H$)(CDCl$_3$): 6.67 (1, d, J, 8.1, 2-H), 6.59 (1, d, J, 8.2, 1-H), 5.79 (1, dd, J, 6.3 & 1.0, 7-H), 5.57 (1, d, J, 6.3, 8-H), 5.48 (1, s, 5-H), 3.85 (3, s, OCH$_3$), 3.66 (1, d, J, 7.0, 9-H), 3.35 (1, d, J, 18.2, 10-H$_\beta$), 2.90 (1, td, J, 12.8 & 3.7, 16-H$_a$), 2.74 (1, dd, J, 18.4 & 7.4, 10-H$_\alpha$), 2.65 (1, dm, J, 13.2, 16-H$_e$), 2.48 (3, s, NCH$_3$), 2.31 (1, td, J, 12.7 & 5.2, 15-H$_a$), 2.20 (3, s, OAc), and 1.75 (1, dm, J, 12.7, 15-H$_e$).

EXAMPLE 3
Preparation of 14-hydroxycodeinone (1-4) from codeinone dienol acetate (1-3) by H$_2$O$_2$ A solution of codeinone dienol acetate (1.12 g, 3.3 mmol), formic acid (90% aqueous solution, 0.80 g, 15.6 mmol), hydrogen peroxide (31% aqueous solution, 0.90 g, 8.2 mmol), and water (1.60 g) was allowed to stir at 40–42° C. for 4.5 hr, cooled to room temperature, basified with concentrated NH$_4$OH, and extracted with CH$_2$Cl$_2$ (50 ml). The extract was washed with water (20 ml), dried over anhydrous Na$_2$SO$_4$, and evaporated to dryness in vacuo to give 14-hydroxycodeinone (0.80 g, 78% yield). The R$_f$ value in TLC, the IR spectrum and the NMR spectrum of the product were comparable to those obtained from an authentic sample.

EXAMPLE 4
Preparation of 14-hydroxycodeinone (1-4) from codeinone dienol acetate (1-3) by MCPBA A solution of codeinone dienol acetate (1.16 g, 3.4 mmol), oxalic acid (0.70 g, 7.4 mmol) and 3-chloroperoxybenzoic acid (57~86%, 0.83 g) in glacial acetic acid (10.02 g) was allowed to stir at room temperature for 6 hr, basified with concentrated NH$_4$OH, and extracted with CH$_2$Cl$_2$ (50 ml). The extract was washed with water (10 ml), dried over anhydrous Na$_2$SO$_4$, and evaporated to dryness in vaco to give a crude product (1.29 g), which was chromatographed on silica gel to give pure 14-hydroxycodeinone (0.76 g, 72% yield). IR (KBr)(v, cm$^{-1}$): 3300 (m, b, —OH), 1670 (s, sharp, C=C—C=O), NMR ($\delta_H$)(CDCl$_3$): 6.69 (1, d, J, 8.2, 2-H), 6.60 (1, d, J, 8.2, 1-H), 6.60 (1, d, J, 10.1, 8-H), 6.17 (1, dd, J, 10.1 & 0.3, 7-H), 4.69 (1, s, 5-H), 3.85 (3, s, OCH$_3$), 3.23 (1, d, J, 18.6, 10-H$_\beta$), 3.03 (1, d, J, 6.0, 9-H), 2.63–2.16 (1, m, 15-H$_a$), 2.63–2.16 (2, m, 16-H$_a$ & 16-He), 2.6–2.4 (1, b, —OH), 2.50 (1, dd, J, 18.5 & 4.9, 10-H$_\alpha$), 2.45 (3, s, NCH$_3$), 1.68 (1, dm, J, 12.7, 15-H$_e$). The R$_f$ value in TLC, the IR spectrum and the NMR spectrum of the product were consistent with those obtained from an authentic sample.

EXAMPLE 5
Preparation of 14-hydroxycodeinone (1-4) from codeinone (1-2) by H$_2$O$_2$ A solution of codeinone (0.503 g, 1.7 mmol), formic acid (0.7 ml) and H$_2$O$_2$ (1.0 ml) in Water (1.4 ml) was allowed to stir at 50–55° C. for 7 hr. The mixture was cooled, basified with NH$_4$OH, and extracted with CHCl$_3$ (3×15 ml). The extract was washed with water, dried over anhydrous Na$_2$SO$_4$ and evaporated to dryness in vacuo to give a solid residue (0.17 g), which is comparable to 14-hydroxycodeinone in its IR spectrum, NMR spectrum, and the R$_f$ value in TLC with those of an authentic sample.

EXAMPLE 6
Preparation of oxycodone (1-5) from codeinone dienol acetate (1-3)

A solution of codeinone dienol acetate (0.50 g, 1.48 mmol), formic acid (0.7 ml), hydrogen peroxide (0.43 g, 30%, 3.79 mmol), and water (1.4 ml) was heated at 43–44° C. for 6 hr and cooled to rt. over night. To the solution was added 5% Pd/C (80 mg) and hydrogenated at rt. under 28 psi of hydrogen gas for 18 hr. The reaction mixture was filtered. The filtrate was basified with NH$_4$OH and extracted with methylene chloride. The extract was washed with water, dried over anhydrous sodium sulfate, and evaporated in vacuo to dryness to give oxycodone (0.40 g, 85% yield). The R$_f$ value in TLC and the IR spectrum of the product were comparable to those obtained from an authentic sample.

B. Synthesis of Oxymorphone From Morphine Through 3-Acetylmorphinone

EXAMPLE 7
Preparation of 3-acetylmorphine(2-1)

A mixture of morphine (23.63 g, 83 mmol), NaHCO$_3$ (28.2 g, 336 mmol), Ac$_2$O (8.69 g, 85 mmol) in toluene (500 ml) and CH$_3$CN (900 ml) was heated at reflux for 21 hrs. The reaction mixture was evaporated to dryness in vacuo. To the residue was added water (80 ml) and extracted with chloroform (500 ml). The extracts were dried, combined and evaporated to dryness in vacuo to obtain a residue, which was chromatographed on silica gel (column: d=6 cm, l=8 cm, packed with 141 g of silica gel; solvent system: 5–10% MeOH in CH$_2$Cl$_2$) to yield 3-acetylmorphine (27 g, 100% yield). IR (KBr)(v, cm$^{-1}$): 3500 (m, sharp, —OH), 1750 (s, sharp, AcO); NMR ($\delta_H$)(CDCl$_3$): 6.73 (1, d, J, 8.1, 2-H), 6.57 (1, d, J, 8.1, 1-H), 5.74 (1, dm, J, 10.1, 7-H), 5.25 (1, dm, J, 9.9, 8-H), 4.91 (1, d, J, 6.9, 5-H), 4.25–4.10 (1, m, 6-H), 3.50–3.35 (1, m, 9-H), 3.05(1, d, J, 19.1, 10-H$_\beta$), 2.8–2.7 (1, m, 14-H), 2.85–2.60 (1, m, 16-H$_e$), 2.50–2.25 (1, m, 16-H$_a$), 2.45 (3, s, NCH$_3$), 2.5–2.2 (1, m, 10-H$_\alpha$), 2.28 (3, s, AcO), 2.06 (1, td, J, 12.1 & 5.0, 15-H$_a$), 2.0–1.85 (1, m, 15-H$_e$).

EXAMPLE 8
Preparation of 3-acetylmorphinone (2-2)

To a solution of DMSO (14.42 g, 158 mmol) in CH$_2$Cl$_2$ at –78° C. was added oxalyl chloride (11.68 g, 92 mmol) in CH$_2$Cl$_2$ (50 ml) in 18 min. The solution was allowed to stir for 15 min. A solution of 3-acetylmorphine (20.02 g, 61 mmol) in CH$_2$Cl$_2$ (100 ml) was added dropwise in one hr. The resulting mixture was allowed to stir at –78° C. for 2 hrs. Et$_3$N (50 ml) was added. The reaction mixture was allowed to warm-up to rt., washed with water (4×100 ml), dried over anhydrous Na$_2$SO$_4$, and evaporated to dryness in vacuo to obtain a dark residue (25.8 g), which was chromatographed on silica gel (column: d=5 cm, l=10 cm; solvent system: 5% MeOH in CHCl$_3$) to give 3-acetylmorphinone (14.5 g, 73% yield). IR (KBr)(v, cm$^{-1}$): 1760 (s, sharp, AcO), 1670 (s, sharp, C=C—C=O); NMR ($\delta_H$)(CDCl$_3$): 6.81 (1, d, J, 8.1, 2-H), 6.65 (1, d, J, 8.2, 1-H), 6.62 (d, J, 10.2, 8-H), 6.08 (1, dd, J, 10.3 & 2.8, 7-H), 4.73 (1, s, 5-H), 3.53–3.40 (1, m, 9-H), 3.25–3.20 (1, m, 14-H), 3.14 (1, d, J, 18.9, 10-H$_\beta$), 2.63 (1, dm, J, 12.1, 16-H$_e$), 2.46 (3, s, NCH$_3$), 2.5–2.2 (1, m, 10-H$_\alpha$), 2.5–2.2 (1, m, 16-H$_a$), 2.27 (3, s, AcO), 2.09 (1, td, J, 12.9 & 4.8, 15-H$_a$), 1.95–1.80 (1, m, 15-H$_e$).

EXAMPLE 9
Preparation of 3-acetylmorphinone dienol acetate (2-3)

A solution of 3-acetylmorphinone (3.25 g, 10 mmol) and acetic anhydride (29.1 g) was stirred at 99° C. for 15 hr. The resulting mixture was basified with aqueous sodium bicarbonate, and extracted with CH$_2$Cl$_2$. The extract was washed with water, dried over anhydrous sodium sulfate, and evaporated in vacuo to dryness. The residue (3.95 g) was chromatographed on silica gel to give 3-acetylmorphinone dienol acetate (1.5 g, 41% yield). IR (KBr)(v, cm$^{-1}$): 2900 (m, sharp), 1750 (s, sharp, AcO); NMR ($\delta_H$)(CDCl$_3$): 6.78 (1, d, J, 8.1, 2-H), 6.62 (1, d, J, 8.1, 1-H), 5.78 (1, dd, J, 6.3 & 0.9, 7-H), 5.55 (1, d, J, 6.3, 8-H), 5.50 (1, s, 5-H), 3.63 (1, d, J, 6.9, 9-H), 3.34 (1, d, J, 18.3, 10-H$_\beta$), 2.85 (1, td, J, 12.8 & 3.6, 16-H$_a$), 2.72 (1, dd, J, 18.5 & 6.5, 10-H$_\alpha$), 2.63 (1, dm, J, 12.3, 16-H$_e$), 2.46 (3, s, NCH$_3$), 2.28 (3, s, 3-AcO), 2.19 (3, s, 6-AcO), 2.25–2.10 (1, m, 15-H$_a$), 1.76 (1, dm, J, 12.7, 15-H$_e$); MS (El), m/e (%): 367 (M$^+$, 52), 325 (89, [M—CH$_2$CO]$^+$), 283 (68, [M-2CH$_2$CO]$^+$), 43 (100, [CH$_3$CO]$^+$).

EXAMPLE 10
Preparation of 3-acetylmorphinone dienol acetate (2-3)

A mixture of 3-acetylmorphinone (6.05 g, 18.6 mmol), NaHCO$_3$ (2.12 g, 26 mmol), and Ac$_2$O (40.3 g, 395 mmol) in toluene (110 ml) was heated at 75° C. for 29 hrs. The cooled reaction mixture was chromatographed on silica gel (column: d=5 cm, packed with 100 g of dry silica gel; solvent systems: 700 ml of CH$_2$Cl$_2$ and then 5% MeOH in CH$_2$Cl$_2$) to obtain 3-acetylmorphinone dienol acetate (6.71 g, 99% yield). The R$_f$ value in TLC, the IR spectrum, and the NMR spectrum of the product were comparable to those obtained from an authentic sample.

EXAMPLE 11
Preparation of 3-acetyl-14-hydroxymorphinone (2-4) from 3-acetylmorphinone dienol acetate (3-3) by MCPBA A solution of 3-acetylmorphinone dienol acetate (1.42 g, 3.88 mmol), oxalic acid (0.71 g, 7.89 mmol), meta-chloroperbenzoic acid (0.63 g, 57–86% pure) in AcOH was allowed to stir at rt. overnight, basified with conc. NH$_4$OH, extracted with CH$_2$Cl$_2$ (3×70 ml). The extracts were dried, combined, and evaporated to dryness in vacuo to give a solid residue, which was chromatographed on silica gel (column: d=2 cm, packed with 28 g of silica gel, eluting solvent: 5% MeOH in CH$_2$Cl$_2$ to give 3-acetyl-14-hydroxymorphinone (1.12 g, 85% yield). The R$_f$ value in TLC and the IR spectrum of the product were comparable to those obtained from an authentic sample.

EXAMPLE 12
Preparation of 3-acetyl-14-hydroxymorphinone (2-4) from 3-acetylmorphine dienol acetate (3–3) by H$_2$O$_2$ A solution of 3-acetylmorphinone dienol acetate (1.5 g, 4.1 mmol), formic acid (10 ml), water (0.5 ml), and hydrogen peroxide (0.55 ml, 30%, 4.8 mmol) was stirred at 40–47° C. for 5.5 hr. The reaction solution was basified with sodium carbonate (12 g, 115 mmol) and extracted with CH$_2$Cl$_2$ (3×40 ml). The combined extract was dried over anhydrous sodium sulfate and evaporated in vacuo to dryness. The residue (1.06 g) was chromatographed on silica gel to give 3-acetyl-14-hydroxymorphinone (0.75 g, 57% yield). IR (KBr)(v, cm$^{-1}$): 3300 (m, b, —OH), 2900 (m, sharp), 1757 (s, sharp, 3-AcO), 1670 (s, sharp, C=C—C=O); NMR ($\delta_H$)(CDCl$_3$): 6.82 (1, d, J, 8.2, 2-H), 6.67 (1, dd, J, 8.2 & 0.9, 1-H), 6.61 (1, dd, J, 10.0 & 0.7, 8-H), 6.18 (1, dd, J, 10.0 & 0.3, 7-H), 5.22–3.82 (1, b, —OH), 4.73 (1, s, 5-H), 3.26 (1, d, J, 18.9, 10-H$_\beta$), 3.05 (1, d, J, 6.0, 9-H), 2.66–2.20 (2, m, 16-H$_a$ & 16-H$_e$), 2.66–2.20 (1, m, 15-H$_a$) 2.56 (1, dd, J, 19.7 & 6.0, 10-H$_\alpha$), 2.45 (3, s, NCH$_3$), 2.26 (3, s, -A$_c$O), 1.72 (1, dm, J, 13.1, 15-H$_e$); MS (El), m/e (%): 341 (M$^+$, 54), 299 (67, [M—CH$_2$CO]$^+$),70 (100, [CH$_2$=CH—CH=CH—OH]$^+$).

EXAMPLE 13
Preparation of 3-acetyloxymorphone (2-5)

A mixture of 3-acetyl-14-hydroxymorphinone (0.34 g, 1 mmol) and Pd-C (5%, 0.8 g) in ethanol (50 ml) was hydrogenated in a Parr hydrogenator with hydrogen gas (28) at rt. for 3 hr. The reaction mixture was filtered through celite. The filtrate was evaporated in vacuo to give 3-acetyloxymorphone (0.28 g, 82% yield). IR (KBr)(v, cm$^{-1}$): 3400 (s, b, —OH), 2900 (m, sharp), 1760 (s, sharp, AcO), 1720 (s, sharp, C=O); NMR ($\delta_H$)(CDCl$_3$): 6.86 (1, d, J, 8.2, 2-H), 6.68 (1, d, J, 8.2, 1-H), 5.29 (1, s, b, —OH), 4.67 (1, s, 5-H), 3.19 (1, d, J, 18.9, 10-H$_\beta$), 3.01 (1, dd, J, 14.6 & 5.3, 7-H$_a$), 2.92 (1, d, J, 5.5, 9-H), 2.59 (1, dd, J, 18.9 & 6.0, 10-H$_\alpha$), 2.42 (3, s, NCH$_3$), 2.60–2.15 (1, m, 7-H$_e$), 2.60–2.15 (1, m, 15-H$_a$), 2.60–2.15 (2, m, 16-H$_a$ & 16-H$_e$), 2.30 (3, s, AcO), 1.88 (1, ddd, J, 13.3, 5.2 & 3.0, 8-H$_e$), 1.62 (1, td, J, 13.8 & 3.6, 8-H$_a$), 1.57 (1, dm J, 13.4, 15-H$_e$); MS (El), m/e (%): 343 (M$^+$, 1.6), 301 (100, [M—CH$_2$CO]$^+$), 70 (57, [CH$_2$=CH—CH=CH—OH]$^+$).

EXAMPLE 14
Preparation of oxymorphone from 3-acetyloxymorphone (2-6)

A solution of 3-acetyloxymorphone (0.18 g, 0.52 mmol) and sodium carbonate (0.13 g, 1.2 mmol) in methanol (5 ml) and water (0.7 ml) was stirred at rt. for 4 hr. The reaction mixture was evaporated in vacuo to remove methanol, added water (20 ml) and extracted with chloroform (4×20 ml). The combined extract was dried over anhydrous sodium sulfate, and evaporated in vacuo to dryness to give oxymorphone (0.127 g, 85% yield). IR (KBr)(v, cm$^{-1}$): 3340 (m, b, —OH), 2900 (m, sharp), 1715 (s, sharp, C=O); NMR ($\delta_H$)(CDCl$_3$): 6.71 (1, d, J, 8.2, 2-H), 6.59 (1, d, J, 8.2, 1-H), 5.55–4.10 (2, b, —OH), 4.67 (1, s, 5-H), 3.14 (1, d, J, 18.8, 10-H$_\beta$), 3.04 (1, td, J, 14.4 & 5.3, 7-H$_a$), 2.86 (1, d, J, 5.8, 9-H), 2.60–2.15 (1, m, 7-H$_e$), 2.60–2.15 (2, m, 16-H$_a$ & 16-H$_e$), 2.52 (1, dd, J, 18.2 & 5.8, 10-H$_\alpha$), 2.50–2.15 (1, m, 15-H$_a$), 2.40 (3,s, NCH$_3$), 1.87 (1, ddd, J, 13.4, 5.1 & 2.8, 8-H$_e$), 1.62 (1, td, J, 13.9 & 3.5, 8-H$_a$), 1.58(1, dm, J, 13.4, 15-H$_e$).

C. Synthesis of Oxymorphone From Morphine Through 3-Benzylmorphinone

EXAMPLE 15
Preparation of 3-benzylmorphine (3-1)

A solution of morphine (14.27 g, 50.0 mmol), NaOH (2.04 g, 51.0 mmol), and benzylbromide (8.47 g, 49.5 mmol) in MeOH (150 ml) and water (50 ml) was stirred at rt. for 3.5 hr., evaporated in vacuo to remove MeOH. The residue was extracted with CH$_2$Cl$_2$ (120 ml). The extract was dried over anhydrous Na$_2$SO$_4$ and evaporated in vacuo to dryness to give a crude residue, which was chromatographed on silica gel (column: d=6.5 cm, l=10.5 cm; eluting solvent: 15% MeOH in $CH_2Cl_2$) to obtain 3-benzylmorphine (13.1 g, 70% yield). The $R_f$ value in TLC and the IR spectrum of the product were comparable to those obtained from an authentic sample.

EXAMPLE 16
Preparation of 3-benzylmorphinone (3-2) by Swern oxidation

To a solution of dimethyl sulfoxide (3.75 g, 48 mmol) in $CH_2Cl_2$ (15 ml) at −78° C., was added a solution of oxalyl chloride (3.8 g, 30 mmol) in $CH_2Cl_2$ (5 ml) in 20 min. It was allowed to stir for another 20 min. To this solution at −78° C., was added a solution of 3-benzylmorphine (6.0 g, 16 mmol) in $CH_2Cl_2$ (15 ml) in 45 min. Then, the reaction mixture was stirred at −78° C. for 3 hr., added triethylamine (17 ml), warmed up to rt., washed with water (8×100 ml), dried over anhydrous sodium sulfate, and evaporated in vacuo to dryness to give 3-benzylmorphinone (about 65% yield). The $R_f$ value in TLC and the IR spectrum of the product were comparable to those obtained from an authentic sample.

EXAMPLE 17
Preparation of 3-benzylmorphinone dienol acetate (3-3)

A mixture of 3-benzylmorphinone (6.0 g, 16.1 mmol), acetic anhydride (47.5 g, 466 mmol), sodium acetate (2.65 g), sodium carbonate (5.2 g), and DMAP(about 0.3 g) was heated at 95° C. for 17 hr., basified with aqueous sodium bicarbonate solution to pH 9.0, and extracted with $CH_2Cl_2$. The extract was washed with water, dried over anhydrous sodium sulfate, evaporated off the solvent in vacuo to give a crude product (9 g), which was chromatographed on silica gel to obtain 3-benzylmorphinone dienol acetate (2.6 g, 39% yield). IR (KBr)(v, cm$^{-1}$): 2900 (m, sharp), 1750 (s, sharp, C=C—C=C—OAc); NMR ($\delta_H$)(CDCl$_3$): 7.53–7.15 (5, m, —C$_6$H$_5$), 6.69 (1, d, J, 8.2, 2-H), 6.53 (1, d, J, 8.2, 1-H), 5.79 (1, dd, J, 6.2 & 0.9, 7-H), 5.58 (1, d, J, 6.4, 8-H), 5.49 (1, s, 5-H), 5.14 (2, s, OCH$_2$Ph), 3.70 (1, d, J, 7.0, 9-H), 3.33 (1, d, J, 18.1, 10-H$_\beta$), 2.93 (1, td, J, 12.9 & 3.7, 16-H$_a$), 2.76 (1, dd, J, 18.5 & 6.7, 10-H$_\alpha$), 2.68 (1, dm, J, 13.5, 16-H$_e$), 2.49 (3, s, NCH$_3$), 2.32 (1, td, J, 12.8 & 5.1, 15-H$_a$), 2.18 (3, s, AcO), 1.74 (1, dm, J, 12.8, 15-H$_e$); MS (EI), m/e (%): 415 (M$^+$, 15), 324 (40, [M—CH$_2$Ph]$^+$), 282 (48, [M—CH$_2$Ph-CH$_2$CO]$^+$), 91 (100, [CH$_2$Ph]$^+$).

EXAMPLE 18
Preparation of 3-benzyl-14 hydroxymorphinone (3-4) from 3-benzylmorphinone dienol acetate (3-3) by MCPBA in HOAc A solution of 3-benzylmorphinone dienol acetate (2.6 g, 6.26 mmol), oxalic acid (1.15 g, 12.8 mmol), and 3-chloroperbenzoic acid (1.85 g, 57–86%) in glacial acetic acid(20 ml) was stirred at rt. for 15.5 hr., basified with aqueous sodium bicarbonate solution to pH 9, extracted with $CH_2Cl_2$. The extract was washed with water, dried over anhydrous sodium sulfate, and evaporated in vacuo to dryness to obtain a crude product (2.3 g), which was chromatographed on silica gel to give 3-benzyl-14-hydroxymorphinone (1.43 g, 59% yield). IR (KBr, cm$^{-1}$): 3280 (m, b, OH), 2900 (m sharp), 1670 (s, sharp, C=C—C=O); NMR ($\delta_H$)(CDCl$_3$): 7.44–7.20 (5, m, —C$_6$H$_5$), 6.71 (1, d, J, 8.1, 2-H), 6.59 (1, d, J, 10.1, 8-H), 6.55 (1, d, J, 8.2, 1-H), 6.16 (1, dd, J, 10.1 & 0.5, 7-H), 5.16 (2, s, OCH$_2$Ph), 4.71 (1, s, 5-H), 3.20 (1, d, J, 18.6, 10-H$_\beta$), 3.02 (1, d, J, 6.0, 9-H), 2.70–2.40 (1, b, —OH), 2.60–2.35 (2, m, 16-H$_a$ & 16-H$_e$), 2.53 (1, dd, J, 19.4 & 6.0, 10-H$_\alpha$), 2.5–2.2 (1, m, 15-H$_a$), 2.43 (3, s, NCH$_3$); 1.67 (1, dm, J, 12.7, 15-H$_e$).

EXAMPLE 19
Preparation of 3-benzyl-14 hydroxymorphinone (3-4) from 3-benzylmorphinone dienol acetate (3-3) by $H_2O_2$ in formic acid and water A solution of 3-benzyimorphinone dienol acetate (1.4 g, 3.37 mmol), formic acid (10 ml, 90%), and hydrogen peroxide (0.48 ml, 30%, 4.2 mmol) was stirred at 38~47° C. for 4 hr., basified with sodium carbonate to pH 8, extracted with $CH_2Cl_2$. The extract was washed with aqueous sodium bicarbonate solution, dried over anhydrous sodium sulfate, and evaporated in vacuo to dryness. The residue (1.0 g) was chromatographed on silica gel to give 3-benzyi-14 hydroxymorphinone (0.7 g, 54% yield). The $R_f$ value in TLC and the IR spectrum of the product were comparable to those obtained from an authentic sample.

EXAMPLE 20
Preparation of oxymorphone (3-5) from 3-benzyl-14 hydroxymorphinone (3-4)

A mixture of 3-benzyl-14-hydroxymorphinone (0.9 g, 2.31 mmol) and 5% Pd-C (0.65 g) in ethanol (50 ml) was hydrogenated in a Parr hydrogenator with hydrogen gas (30 psi) at rt. for 4 hr., and filtered through celite. The filtrate was evaporated in vacuo to give oxymorphone (0.65 g, 94% yield). IR (KBr)(v, cm$^{-1}$): 3200 (s, b, —OH), 2920 (m, sharp), 1720 (s, sharp, C=O); NMR ($\delta_H$)(CDCl$_3$): 6.72 (1, d, J, 8.1, 2-H), 6.58 (1, d, J, 8.2, 1-H), 5.38 (2, b, —OH), 4.70 (1, s, 5-H), 3.15 (1, d, J, 18.6, 10-H$_\beta$), 3.04 (1, td, J, 14.5 & 5.3, 7-H$_a$), 2.88 (1, d, J, 5.8, 9-H), 2.54 (1, dd, J, 19.6 & 5.7, 10-H$_\alpha$), 2.55–2.15 (2, m, 16-H$_a$ & 16-H$_e$), 2.45–2.15 (2, m, 15-H$_a$ & 7-H$_e$), 2.41 (3, s, NCH$_3$), 1.88 (1, ddd, J, 13.3, 5.2 & 3.0, 8-H$_e$), 1.67 (1, td, J, 14.4 & 3.5, 8-H$_a$), 1.73–1.50 (1, m, 15-H$_e$).

Synthesis of Noroxymorphone From Morphine Through 3,17-Dibenzylnormorphine

EXAMPLE 21
Preparation of 3-benzylmorphine (4-1) (see also 3-1))

To a suspension of morphine (10.0 g, 35.1 mmol) in THF (200 ml), was added benzyi bromide (5.5 ml, 98%, 45.3 mmol) and sodium hydroxide (1.48 g, 37.0 mmol) at 0° C. The reaction mixture was stirred overnight. The reaction temperature rose gradually to rt. during the process. THF in the reaction mixture was removed on a rotary evaporator. The residue was dissolved in $CH_2Cl_2$ (150 ml) and water (50 ml). The organic layer was separated. The aqueous layer was extracted with $CH_2Cl_2$ (3×50 ml). The combined organic layer was dried over anhydrous sodium sulfate, evaporated in vacuo to obtain a crude product (13 g), which was dissolved in $CH_2Cl_2$ and loaded onto a silica gel column (3×30 cm). The column was first eluted with 3% methanol in $CH_2Cl_2$, followed by 5% methanol in $CH_2Cl_2$. Pure fractions were combined to obtain 3-benzylmorphine (7.9 g, 60% yield). IR (KBr)(v, cm$^{-1}$): 3540 (m, sharp, —OH), 3020 (m, sharp), 2900 (s, sharp), 1600 (m, sharp); NMR ($\delta_H$)(CDCl$_3$): 7.50–7.20 (5, m, —C$_6$H$_5$), 6.70 (1, d, J, 8.1, 2-H), 6.51 (1, dd, J, 8.1 & 0.9, 1-H), 5.65 (1, drn, J, 9.9, 7-H), 5.26 (1, dt, J, 9.9 & 2.5, 8-H), 5.12 (2, AB, OCH$_2$Ph), 4.85 (1, dd, J, 6.6 & 1.2, 5-H), 4.22–4.05 (1, m, 6-H), 3.32 (1, dd, J, 6.2 & 3.3, 9-H), 3.02 (1, d, J, 18.6, 10-H$_\beta$), 2.75–2.65 (1, m, 14-H), 2.75–2.65 (1, b, —OH), 2.58 (1, dm, J, 12.0, 16-H$_e$), 2.5–2.3 (1, m, 16-H$_a$), 2.42 (3, s, N—CH$_3$), 2.27 (1, dd, J, 18.6 & 6.6, 10-H$_\alpha$), 2.05 (1, td, J, 12.1 & 5.3, 15-H$_a$), 1.85 (1, dm, J, 12.5, 15-H$_e$).

EXAMPLE 22
Preparation of 6-acetyl-3-benzylmorphine (4-2)

To a solution of 3-benzylmorphine (12.7 g, 33.9 mmol) in $CH_2Cl_2$ (300 ml), was added triethylamine (10 ml, 99%, 71.2 mmol), acetic anhydride (7.5 ml, 99%, 78.6 mmol), and 4-dimethylaminopyridine (0.3 g). The reaction mixture was heated under reflux for 2 hr, cooled with an ice —$H_2O$ bath, then transferred to a separatory funnel, and washed with cold 10% aqueous $NaHCO_3$ solution (3×100 ml). The organic layer was separated and dried over anhydrous $Na_2SO_4$. Removal of solvent gave 6-acetyl-3-benzylmorphine (13.87 g, 96% yield). IR (KBr)(v, cm$^{-1}$): 2900 (m, sharp), 1727 (s, sharp, AcO); NMR ($\delta_H$)(CDCl$_3$): 7.47–7.20 (5, m, —$C_6H_5$), 6.68 (1, d, J, 8.1, 2-H), 6.48 (1, d, J, 8.2, 1-H), 5.63 (1, dm, J, 10.1, 7-H), 5.43 (1, dt, J, 10.1 & 2.3, 8-H), 5.25–5.1 (1, m, 6-H), 5.14 (2, s, —OCH$_2$Ph), 5.10 (1, dd, J, 6.7 & 1.1, 5-H), 3.34 (1, dd, J, 6.0 & 3.3, 9-H), 3.01 (1, d, J, 18.6, 10-H$_\beta$), 2.79–2.70 (1, m, 14-H), 2.59(1, dd, J, 12.1 & 3.4, 16-H$_e$), 2.43 (3, s, N—CH$_3$), 2.37 (1, td, J, 11.8 & 3.6, 16-H$_a$), 2.27 (1, dd, J, 18.8 & 6.6, 10-H$_\alpha$), 2.10 (3, s, AcO), 2.04 (1, td, J, 11.9 & 5.1, 15-H$_a$), 1.86 (1, dm, J, 12.5, 15-H$_e$).

EXAMPLE 23
Preparation of 3,17-dibenzylnormorphine (4-4) from 6-acetyl-3-benzylmorphine To a solution of 6-acetyl-3-benzylmorphine (13.7 g, 32.1 mmol) and proton sponge (1.2 g) in 1,2-dichloroethane (50 ml) was added 1-chloroethyl chloroformate (ACE-Cl, 4.5 ml, 41.7 mmol) at 0° C. The reaction mixture was heated under reflux for 30 min. The reaction mixture was cooled to rt., added methanol (30 ml) and conc. HCl (a few drops), and heated under reflux for another 30 min. Precipitate came out. Then, methanol (50 ml), $Na_2CO_3$ (10.2 g, 96.2 mmol) and benzyl bromide (4.7 ml, 98%, 38.7 mmol) were added at rt. The reaction mixture was stirred at rt. over the weekend. The solvents were removed on a rotary evaporator. Ethyl acetate (100 ml) and water (100 ml) was added. The organic layer was separated and washed with 10% aqueous $NaHCO_3$ solution (2×50 ml), then dried over anhydrous $Na_2SO_4$. Removal of solvent gave a crude product (7.5 g), which was dissolved in $CH_2Cl_2$ and loaded onto a column (5×16 cm, packed with silica gel in $CH_2Cl_2$). The column was eluted first with $CH_2Cl_2$ and then with $CH_2Cl_2$/EtOAc (50/50) to give 3,17-dibenzylnormorphine (13.3 g, 92% yield from 6-acetyl-3-benzylmorphine). IR (KBr)(v, cm$^{-1}$): 3440 (m, b, —OH), 3020 (m, sharp), 2900 (m, sharp), 1600 (m, sharp); NMR ($\delta_H$)(CDCl$_3$): 7.50–7.20 (10, m, —$C_6H_5$), 6.70 (1, d, J, 8.2, 2-H), 6.52 (1, d, J, 8.1, 1-H), 5.58 (1, dm, J, 9.9, 7-H), 5.21 (1, dm, J, 9.9, 8-H), 5.12 (2, AB, —OCH$_2$Ph), 4.85 (1, dd, J, 6.4 & 1.2, 5-H), 4.25–4.05 (1, m, 6-H), 3.69 (2, AB, N—CH$_2$Ph), 3.37 (1, dd, J, 6.2 & 3.3, 9-H), 3.06 (1, d, J, 18.6, 10-H$_\beta$), 2.80–2.55 (1, b, —OH), 2.75–2.65 (1, m, 14-H), 2.61 (1, dd, J, 12.1 & 4.0,16-H$_e$), 2.46 (1, td, J, 11.9 & 3.7, 16-H$_a$), 2.29 (1, dd, J, 18.6 & 6.4, 10-H$_\alpha$), 2.04 (1, td, J, 11.7 & 5.3, 15-H$_a$), 1.86 (1, dm, J, 12.5, 15H)$_e$).

EXAMPLE 24
Preparation of 3,17-dibenzylmormorphinone (4-5)

To a solution of DMSO (5.87 g, 75.1 mmol) in $CH_2Cl_2$ (40 ml) at −78° C., was added a solution of oxalyl chloride (4.7 g, 37.6 mmol) in $CH_2Cl_2$ (15 ml) in 20 min. The mixture was stirred for 10 min. and then was added a solution of 3,17-dibenzylnormorphine (11.3 g, 25.1 mmol) in $CH_2Cl_2$ (20 ml) in 40 min. The mixture was stirred at −78° C. for 2 hr, and then Et$_3$N (13 ml) was added. It was allowed to warm up to rt., transferred to a separatory funnel, washed with water (10×100 ml), dried over anhydrous sodium sulfate, and evaporated in vacuo to dryness to give 3,17-dibenzylnormorphinone (11.0 g, 98% yield). IR (KBr)(v, cm$^{-1}$): 3020 (m, sharp), 2900 (m, sharp), 1670 (s, sharp, —C=C—C=O); NMR ($\delta_H$)(CDCl$_3$): 7.51–7.16 (10, m, —$C_6H_5$), 6.71 (1, d, J, 8.2, 2-H), 6.56 (1, d, J, 8.2,1-H), 6.56 (1, d, J, 10.5, 8-H), 6.05 (1, dd, J, 10.2 & 2.9, 7-H), 5.17 (2, s, OCH$_2$Ph), 4.70 (1, s, 5-H), 3.71 (2, AB, NCH$_2$Ph), 3.43 (1, dd, J, 5.2 & 3.1, 9-H), 3.23 (1, dd, J, 5.1 & 2.6,14-H), 3.12 (1, d, J, 18.5, 10-H$_\beta$), 2.64 (1, dm, J, 11.8, 16-H$_e$), 2.50–2.25 (1, m, 10-H$_\alpha$), 2.35 (1, td, J, 11.9 & 3.7, 16-H$_a$), 2.05 (1, td, J, 12.0 & 4.9, 15-H$_a$), 1.81 (1, dm, J, 12.1, 15-H$_e$); MS (El), m/e (%): 449 (M$^+$, 5.5), 358 (21, [M—CH$_2$Ph]$^+$), 91 (100, [CH$_2$Ph]$^+$).

EXAMPLE 25
Preparation of 3,17-dibenzylnormorphinone dienol acetate (4-6)

To a mixture of 3,17-dibenzylnormorphinone (3.7 g, 8.2 mmol), CH$_3$CO$_2$Na (2.7 g, 32.9 mmol) and Na$_2$CO$_3$ (10.4 g, 124 mmol), was added Ac$_2$O (26.3 g, 25.8 mmol). The mixture was stirred at 100° C. for 14 hr., cooled, basified to pH 8 with cold aqueous NaHCO$_3$, and extracted with CH$_2$Cl$_2$ (50 ml). The extract was waspd with water (2×100 ml),dried over anhydrous sodium sulfate, evaporated in vacuo to give a crude product (4.6 g), which was dissolved in CH$_2$Cl$_2$ and loaded onto a column (2.4×37 cm, 77 g silica gel, packed in CH$_2$Cl$_2$). The column was eluted with CH$_2$Cl$_2$, and then with a gradient solution of ethyl acetate in hexane to obtain pure 3,17-dibenzylnormorphinone dienol acetate (1.7 g, 42% yield). IR (KBr)(v, cm$^{-1}$): 3020 (m, sharp), 2900 (m, sharp), 1750 (s, sharp, —C=C—C=C—OAc); NMR ($\delta_H$)(CDCl$_3$): 7.50–7.20 (10, m, —$C_6H_5$), 6.68 (1, d, J, 8.2, 2-H), 6.53 (1, d, J, 8.2, 1-H), 5.77 (1, dd, J, 6.2 & 0.8, 7-H), 5.47 (1, d, J, 7.3, 8-H), 5.49 (1, s, 5-H), 5.14 (2, s, OCH$_2$Ph), 3.75 (2, s, NCH$_2$Ph), 3.64 (1, d, J, 7.0, 9-H), 3.32 (1, d, J, 18.0, 10-H$_\beta$), 2.95 (1, td, J, 13.0 & 3.5, 16-H$_a$), 2.75–2.60 (1, m, 16-H$_e$), 2.74 (1, dd, J, 18.7 & 7.1, 10-H$_\alpha$), 2.34 (1, td, J, 12.6 & 4.9, 15-H$_a$), 2.17 (3, s, AcO), 1.70 (1, dm, J, 12.8, 15-H$_e$); MS (El), m/e (%): 491 (M$^+$, 2.9), 400 (8, [M—CH$_2$Ph]$^+$), 458 (10, [M—CH$_2$Ph-CH$_2$CO]$^+$), 91 (100, [CH$_2$Ph]$^+$).

EXAMPLE 26
Preparation of 3,17-dibenzyl-14-hydroxynormorphinone (4-7) from 3,17-dibenzylnormorphinone dienol acetate (4-6) by MCPBA in HOAc To a solution of 3,17-dibenzylnormorphinone dienol acetate (1.4 g, 2.85 mmol) in glacial acetic acid (10 ml) was added oxalic acid (0.5 g, 5.6 mmol) and 3-chloroperbenzoic acid (MCPBA, 0.98 g, 57~86%). The reaction mixture was stirred at rt. for 5 hr., basified to pH 8~9 with NH$_4$OH, extracted with CH$_2$Cl$_2$ (3×50 ml). The combined organic extract was dried over anhydrous sodium sulfate, evaporated in vacuo to dryness to obtain 3,17-dibenzyl-14-hydroxynormorphinone (0.9 g, 68% yield). The R$_f$ value in TLC and the IR spectrum of the product were comparable to those obtained from an authentic sample.

EXAMPLE 27
Preparation of 3,17-dibenzyl-14-hydroxynormorphinone (4-7) from 3,17-dibenzylnormorphinone dienol acetate (4-6) by MCPBA in 90% formic acid To a solution of 3,17-dibenzylnormorphinone dienol acetate (1.54 g, 3.13 mmol) in formic acid (20 ml, 90%), was added 3-chloroperbenzoic acid (MCPBA, 1.02 g, 57~86%). The reaction mixture was stirred at rt. for 17 hr., basified to pH 8 with cold aqueous Na$_2$CO$_3$, and extracted with CH$_2$Cl$_2$. The extract was dried over anhydrous Na$_2$SO$_4$, and evaporated in vacuo to dryness. The residue was chromatographed on silica gel to give 3,17-dibenzyl-14-hydroxynormorphinone (0.86 g, 60% yield). The $R_f$ value in TLC and the IR spectrum of the product were comparable to those obtained from an authentic sample.

EXAMPLE 28

Preparation of 3,17-dibenzyl-14-hydroxynormorphinone (4-7) from 3,17-dibenzylnormorphinone dienol acetate (4-6) by $H_2O_2$ in formic acid and water A solution of 3,17-dibenzylnormorphinone dienol acetate (1.7 g, 3.46 mmol) and $H_2O_2$ (30%, 0.5 ml) in formic acid (90%, 20 ml) was stirred at 37~47° C. for 4 hr basified to pH 8.0 with $NaHCO_3$ and 5% $NaHCO_3$ solution, extracted with $CH_2Cl_2$. The extract was washed with 5% $NaHCO_3$, dried over anhydrous $Na_2SO_4$, and evaporated in vacuo to obtain a crude product, which was chromatographed on silica gel to give pure 3,17-dibenzyl-14-hydroxynormorphinone (0.74 g, 60% yield). IR (KBr)(v, cm$^{-1}$): 3340 (s, b, —OH), 2900 (m, sharp), 1675 (s, sharp, —C=C—C=O); NMR ($\delta_H$) (CDCl$_3$): 7.48–7.15(10, m, —C$_6$H$_5$), 6.73(1, d, J, 8.2, 2-H), 6.58(1, d, J, 8.8, 1-H), 6.53(1, d, J, 10.1, 8-H), 6.14 (1, d, J, 10.1, 7-H), 5.3–4.8 (1, b, —OH), 5.16 (2, s, OCH$_2$Ph), 4.71 (1, s, 5-H), 3.70 (2, s, NCH$_2$Ph), 3.27 (1, d, J, 18.6, 10-H$_\beta$), 3.11 (1, d, J, 5.8, 9-H), 2.70–2.55 (1, m, 16-H$_e$), 2.57 (1, dd, J, 18.5 & 5.7, 10-H$_\alpha$), 2.45 –2.25 (2, m, 15-H$_a$ & 16-H$_a$), 1.68 (1, dm, J, 11.6, 15-H$_e$); MS (EI), m/e (%): 465 (M$^+$, 10), 374 (20, [M—CH$_2$Ph]$^+$), 91 (100, [CH$_2$Ph]$^+$).

EXAMPLE 29

Preparation of 3,17-dibenzyl-14-hydroxynormormhinone (4-7) from 3.17-dibenzylnormorphinone (4-5)

A solution of 3,17-dibenzylnormorphinone (0.875 g, 2.22 mmol), $H_2O_2$ (30%, 0.76 ml), and formic acid (90%, 0.7 ml) in water (0.8 ml) and EtOAc (0.7 ml) was stirred at 41° C. for 7 hr., basified to pH 10 with $Na_2CO_3$ and extracted with $CH_2Cl_2$.(3×20 ml) The combined extract was washed with water, dried over anhydrous $Na_2SO_4$, and evaporated in vacuo to obtain 3,17-dibenzyl-14-hydroxynormorphinone (0.48 g, 53% yield). The $R_f$ value in TLC and the IR spectrum of the product were comparable to those obtained from an authentic sample.

EXAMPLE 30

Preparation of noroxymorphone hydrochloride (4-8) from 3,17-dibenzyl-14-hydroxynormorphinone (4-7)

A mixture of 3,17-dibenzyl-14-hydroxynormorphinone (1.48 g, 35.9 mmol), 5% Pd-C (1.0 g), and conc. HCl (0.5 ml) in ethanol (100 ml) was hydrogenated with a Parr hydrogenator with hydrogen gas (30 PSIG) at rt. for 47 hr., and filtered through celite. The filtrate was evaporated in vacuo to give noroxymorphone hydrochloride (1.05 g, 100% yield). IR (KBr)(v, cm$^{-1}$): 3300 (s, b, —OH, —NH), 2900 (m, sharp), 2430 (m, sharp, NH•HCl), 1710 (s, sharp, C=O); NMR ($\delta_H$)(CDCl$_3$): 10.4–8.0 (2, b, $^+$NH$_2$Cl$^-$), 9.40 (1, s, —OH), 6.69 (1, d, J, 8.1, 2-H), 6.61 (1, d, J, 8.1, 1-H), 6.50 (1, s, —OH), 4.93 (1, s, 5-H), 3.70 (1,d, J, 5.5, 9-H), 3.33 (1, d, J, 19.1, 10-H$_\beta$), 3.15–2.85 (1, m, 7-H$_a$), 3.15–2.85 (2, m, 16-H$_a$ & 16-H$_e$), 2.75–2.24 (1, m, 10-H$_\alpha$), 2.75–2.24 (1, m, 15-H$_a$), 2.10 (1, dm, J, 14.6, 7-H$_e$), 1.96 (1, dm, J, 11.8, 15-H$_e$), 1.64–1.20 (2, m, 8-H$_a$ & 8-H$_e$).

Synthesis of naltrexone from codeine through 17-cyclopropylmethylnorcodeinone and 3-methylnaltrexone

EXAMPLE 31

Preparation of 6-acetyicodeine (5-2)

A solution of codeine (30 g, 100.2 mmol), acetic anhydride (18.4 g, 180.2 mmol), triethylamine (18.25 g, 180.2 mmol) and 4-dimethylaminopyridine (0.5 g) in dry ethyl acetate (620 ml) was stirred at rt. under nitrogen for 12 hr, added saturated aqueous sodium bicarbonate solution until no acetic anhydride detected. The organic portion was separated, in washed with water (3×120 ml), dried over anhydrous sodium sulfate, and evaporated in vacuo to dryness to give 6-acetylcodeine as white solids (34.0 g, 99% yield). IR (KBr)(v, cm$^{-1}$): 1725 (st, sharp, 3-AcO); NMR ($\delta_H$)(CDCl$_3$): 6.66 (1, d, J, 8.2, 2-H), 6.53 (1, d, J, 8.2, 1-H), 5.63 (1, ddd, J, 10.0, 2.4 & 1.0, 7-H), 5.42 (1, dt, J, 9.9 & 2.3, 8-H), 5.22–5.51 (1, m, 6-H), 5.06 (dd, J, 6.7 & 1.0, 5-H), 3.85 (3, s, 3-OCH$_3$), 3.39 (1, dd, J, 6.0 & 3.3, 9-H), 3.03 (1, d, J$_{jem}$, 18.6, 10-H$_\beta$), 2.78 (1, dd, J, 5.2 & 2.6, 14-H), 2.63 (1, dd, J, 11.9 & 4.6, 16-H$_a$), 2.45 (3, s, N—CH$_3$), 2.40 (1, td, J, 12.0 & 3.8, 16-H$_e$), 2.33 (1, dd, J, 18.5 & 6.0, 10-H$_\alpha$), 2.15 (3, s, 6-OAc), 2.06 (1, td, J, 12.0 & 5.0, 15-H$_a$) and 1.85 (1, dm, J, 12.0, 15-H$_e$).

EXAMPLE 32

Preparation of 6-acetylnorcodeine hydrochloride (5-3a)

A solution of 6-acetylcodeine (10.0 g, 29.3 mmol), 1-chloroethyl chloroformate (5.51 g,37.8 mmol), and proton sponge (1.0 g) in methylene chloride (80 ml) was heated at reflux for 80 min. The reaction mixture was evaporated in vacuc to dryness. The residue was chromatographed on silica gel with ethyl acetate to give 6-acetyl-17-(1-chloroethoxycarbonyl)norcodeine as an oil (12.13 g), which was dissolved in methanol with a few drops of conc. HCl. The solution was heated at reflux for 1 hr and evaporated in vacuo to almost dryness. The residue was added hexane and filtered to give 6-acetylnorcodeine hydrochloride (10.7 g, 100% yield). IR (KBr)(v, cm$^{-1}$): 3540 (NH), 1730 (st, sharp, 6-AcO), 2800–2600 (broad) and 2470 (sharp)(NH•HCl); NMR ($\delta_H$)(DMSO-d$_6$): 9.69 (2, s (broad), 17-N$^+$H$_2$ Cl$^-$) 6.76 (1, d, J, 8.2, 2-H), 6.63 (1, d, J, 8.2, 1-H), 5.65 (1, dd, J, 10.1 & 1.8, 7-H), 5.51 (1, dt, J, 10.1 & 2.0, 8-H), 5.16 (1, dt, J, 6.7 & 2.0, 6-H), 5.09 (1, dd, J, 6.7 & 0.8, 5-H), 4.20 (1, dd, J, 5.8 & 3.2, 9-H), 3.77 (3, s, 3-OCH$_3$), 3.28–3.14 (1, m, 16-H$_e$), 3.23 (1, d, J, 18.3, 10-H$_\beta$), 3.07 (1, m), 14-H), 2.88 (1, dd, J, 19.2 & 6.3, 10-H$_\alpha$), 2.73 (1, dd, J, 13.3 & 4.0, 16-H$_a$), 2.24 (1, td, J, 13.4 & 4.6, 15-H$_a$), 2.07 (3, s, 6-AcO) and 1.88 (1, dm, J, 13.4, 15-H$_e$).

EXAMPLE 33

Preparation of norcodeine hydrochloride (5-3b)

A solution of 6-acetylcodeine (10.0 g, 29.3 mmol), 1-chloroethyl chloroformate (5.56 g, 38.1 mmol), and proton sponge (1.0 g) in methylene chloride (50 ml) was heated at reflux for 50 min. The reaction mixture was evaporated in vacuo to about 30 ml. Methanol (25 ml) and concentrated HCl (2 ml) were added. The solution was heated at reflux for 40 min. and evaporated in vacuo to almost dryness. The residue was added hexane and filtered to give norcodeine hydrochloride (8.8 g, 93% yield). IR (KBr), (v, cm$^{-1}$): 3540 (NH), 3380 (6-OH), 2800–2600 (broad) and 2480 (sharp) (NH•HCl); NMR ($\delta_H$)(DMSO-d$_6$): 9.66 (2, s (broad), 17-N$^+$H$_2$ Cl$^-$), 6.72 (1, d, J, 8.2, 2-H), 6.57 (1, d, J, 8.2, 1-H), 5.66 (1, dt, J, 9.9 & 3.0, 7-H), 5.28 (1, dt, J, 9.8 & 3.0, 8-H), 5.10 (1, s (broad), 6-OH), 4.82 (1, dd, J, 6.1 & 1.2, 5-H), 4.15 (2, m, 6-H & 9-H), 3.77 (3, s, 3-OCH$_3$), 3.22 (1, d, J, 19.1, 10-H$_\beta$), 3.21 (1, td, J, 13.2 & 4.1, 16-H$_e$), 3.06 (1, m, 14-H), 2.91 (1, dd, J, 18.5 & 6.3, 10-H$_\alpha$), 2.79 (1, dd, J, 13.0 & 3.9, 16-H$_a$), 2.22 (1, td, J, 13.4 & 4.9, 15-H$_a$) and 1.89 (1, dd, J, 13.6 & 2.7, 15-H$_e$).

EXAMPLE 34
Preparation of 17-cyclopropylmethylnorcodeine (5-4)

A mixture of norcodeine hydrochloride (11.48 g, 27.8 mmol), (chloromethyl)-cyclopropane (5.14 g, 55.6 mmol), sodium carbonate (14.73 g, 139.0 mmol), and potassium iodide (4.61 g, 27.8 mmol) in ethanol (250 ml) was heated at reflux for 20 hr. cooled, and evaporated in vacuo to dryness. The residue was basified with NH$_4$OH, and extracted with methylene chloride. The extract was washed with water and evaporated in vacuo to dryness. The residue (11.7 g) was chromatographed on silica gel with a eluting solvent system of methanol/ethyl acetate (10/90) to give 17-cyclopropylmethylnorcodeine (10.68 g, 91% yield). IR (KBr)(v, cm$^{-1}$): 3300 (sharp, 6-OH); NMR ($\delta_H$)(CDCl$_3$): 6.65 (1, d, J, 8.2, 2-H), 6.523 (1, d, J, 8.2, 1-H), 5.70 (1, dtd, J, 9.9, 1.8 & 1.2, 7-H), 5.29 (1, dt, J, 9.9 & 2.6, 8-H), 4.88 (1, dd, J, 6.6 & 1.2, 5-H), 4.20–4.13(1, m, 6-H), 3.84(3,s, 3-OCH$_3$), 3.66(1, dd, J, 6.3 & 3.3, 9-H), 2.94 (1, d, J, 18.6, 10-H$_\beta$), 2.82 (1, dd, J, 12.1 & 3.9, 16-H$_a$), 2.70 (1, quintet, J, 2.8, 14-H), 2.44 (2, d, J, 6.3, —N—CH$_2$-cyclopropyl), 2.44 (1, overlap, 6-OH), 2.37 (1, td, J, 12.1 & 3.9, 16-H$_e$), 2.30 (1, dd, J, 18.5 & 6.4, 10-H$_\alpha$), 2.09 (1, td, J, 12.4 & 4.9, 15-H$_a$), 1.87 (1, dd, J, 12.5 & 1.8, 15-H$_e$), 0.94–0.80 (1, m, —N—CH$_2$—CH in cyclopropyl ring), 0.54 (2, AB, CH—CH in cyclopropyl ring) and 0.15 (2, AB, CH—CH in cyclopropyl ring).

EXAMPLE 35
Preparation of 17-cyclopropylmethylnorcodeinone (5-5)

To a solution of DMSO (14.50 g, 185.6 mmol) in methylene chloride (80 ml) at −78° C., was added a solution of oxalyl chloride (11.78 g, 92.8 mmol) in methylene chloride (20 ml) in 20 min. After stirring at −78° C. for 20 min., a solution of 17-cyclopropylmethyinorcodeine (9.0 g, 26.5 mmol) in methylene chloride (40 ml) was added dropwise in 50 min. The reaction mixture was stirred at −74 to −76° C. for 3 hr, added triethylamine (9.39 g, 92.8 mmol), allowed to warm up to rt., added methylene chloride (200 ml), washed with water (10×50 ml), and evaporated in vacua to dryness. The residue was mixed with hexane and filtered to give 17-cyclopropylmethyinorcodeinone (8.85 g, 99% yield). IR (KBr)(v, cm$^{-1}$): 1670 (st, sharp, —C=C—C=O); NMR ($\delta_H$)(CDCl$_3$): 6.67 (1, d, J, 8.1, 2-H), 6.65 (1, dt, J, 10.2 & 1.07, 8-H), 6.57 (1, d, J, 8.1, 1-H), 6.07 (1, dt, J, 10.2 & 2.9, 7-H), 4.68 (1, s, 5-H), 3.85 (3, s, 3-OCH$_3$), 3.69 (1, dd, J, 5.2 & 3.0, 9-H), 3.22 (1, dd, J, 5.2 & 2.6, 14-H), 3.00 (1, d, J, 18.3, 10-H$_\beta$), 2.85 (1, dm, J, 11.8, 16-H$_e$), 2.32 (1, dd, J, 18.3 & 5.0, 10-H$_\alpha$), 2.25 (1, td, J, 11.9, 16-H$_a$), 2.07 (1, td, J, 11.9 & 4.6, 15-H$_a$), 1.84 (1, dt, J, 12.0 & 2.0, 15-H$_e$), 2.45 (2, AB, N—CH$_2$-cyclopropyl), 0.93–0.85 (1, m, N—CH$_2$—CH in cyclopropyl ring), 0.55 (2, AB, CH—CH in cyclopropyl ring) and 0.15 (2, AB, CH—CH in cyclopropyl ring); MS (EI), m/e (%): 337 (89.9, [M$^+$]), 296 (17.4, [M—C$_3$H$_5$]$^+$) and 55 (100, [CH$_2$C$_3$H$_5$]$^+$).

EXAMPLE 36
Preparation of 17-cyclopropylmethylnorcodeinone dienol acetate (5-6)

A mixture of 17-cyclopropylmethyinorcodeinone (3.55 g, 10.5 mmol), acetic anhydride (20 ml, 210.4 mmol), sodium acetate (1.3 g, 15.8 mmol), and toluene (6 ml) was heated at 71–73° C. for 14 hr. The reaction mixture was cooled, added methylene chloride (250 ml), water (50 ml), and sodium bicarbonate (73.5 g), stirred for 4 hr, and filtered. The organic portion of the filtrate was separated, washed with water (30 ml), dried over anhydrous sodium sulfate, and evaporated in vacuo to dryness. The residue (3.94 g) was chromatographed on silica gel with 100% ethyl acetate to give 17-cyclopropylmethylnorcodeinone dienol acetate (2.87 g, 72% yield). IR (KBr)(v, cm$^{-1}$): 1750 (st, sharp, —C=C—C=C—OAc); NMR ($\delta_H$)(CDCl$_3$): 6.67 (1, d, J, 8.1, 2-H), 6.58 (1, d, J, 8.1, 1-H), 5.79 (1, dd, J, 6.3 & 0.9, 7-H), 5.55 (1, d, J, 6.3, 8-H), 5.47 (1, s, 5-H), 3.92 (1, d, J, 7.0, 9-H), 3.85 (3, s, 3-OCH$_3$), 3.26 (1, d, J, 17.9, 10-H$_\beta$), 2.89–2.82 (2, m, 16-H$_e$ & 16-H$_a$), 2.75 (1, dd, J, 18.6 & 7.0, 10-H$_\alpha$), 2.49 (2, d, J, 6.4, N—CH$_2$-cyclopropyl), 2.32 (1, td, 12.0 & 4.5, 15-H$_a$), 2.20 (3, s, 6-AcO), 1.71 (1, d, J, 12.2, 15-H$_e$), 0.93–0.86 (1, m, N—CH$_2$—CH in cyclopropyl ring), 0.55 (2, AB, CH—CH in cyclopropyl ring) and 0.15 (2, AB, CH—CH in cyclopropyl ring); MS (EI), m/e (%): 380 (11.2, [M$^+$]), 379 (46.6, [M-H]$^+$), 337 (14.4, [M—CH$_3$CO]$^+$), 282 (15.5, [M—CH$_3$CO—CH$_2$C$_3$H$_5$]$^+$), 241 (33.2, [(M+H)—CH$_3$CO—CH$_2$C$_3$H$_5$—NCH$_2$CH$_2$]$^+$), 55 (100, [CH$_2$C$_3$H$_5$]$^+$) and 43 (29.5, [CH$_3$CO]$^+$).

EXAMPLE 37
Preparation of 17-cyclopropylmethyl-14-hydroxynorcodeinone (5-7) from 17-cyclopropylmethylnorcodeinone (5-5) by H$_2$O$_2$ in HCOOH A solution of 17-cyclopropylmethylnorcodeinone (0.20 g, 0.59 mmol), formic acid (90%, 0.304 g), water (0.504 g), EtOAc (0.27 g), and hydrogen peroxide (30%, 0.17 g) was heated at 42–43° C. for 15 hr, added water (20 ml), basified with Na$_2$CO$_3$ (1.02 g), and extracted with EtOAc (80 ml & 2×20 ml). The combined extract was washed with water, dried over anhydrous sodium sulfate, and evaporated in vacuo to dryness to give 17-cyclopropylmethyl-14-hydroxynorcodeinone (0.10 g, 56% yield). The R$_f$ value in TLC and the IR spectrum of the product were comparable to those obtained from an authentic sample.

EXAMPLE 38
Preparation of 17-cyclopropylmethyl-14-hydroxynorcodeinone (5-7) from 17-cyclopropylmethyinorcodeinone dienol acetate (5-6) by H$_2$O$_2$ in HCOOH A solution of 17-cyclopropylmethylnorcodeinone dienol acetate (1.00 g, 2.63 mmol), formic acid (8 ml, 90%), and hydrogen peroxide(0.37 g, 30%, 3.26 mmol) was heated at 44–45° C. for 6 hr, added water (20 ml) and ethyl acetate (80 ml), basified with sodium bicarbonate. The organic portion was separated, washed with water (15 ml), dried over anhydrous sodium sulfate and evaporated in vacuo to dryness the residue (0.9 g) was chromatographed on silica gel with methanol/methylene chloride (2.5/97.5) to give 17-cyclopropylmethyl-14-hydroxynorcodeinone (0.72 g, 78% yield). IR (KBr)(v, cm$^{-1}$): 1680 (st, sharp, C=C—C=O), 3480–3100 (broad, 3335 (sharp), 14-OH); NMR ($\delta_H$)(CDCl$_3$): 6.70 (1, d, J, 8.2, 2-H), 6.62 (1, dd, J, 10.1 & 0.5, 8-H), 6.59 (1, dd, J, 8.2 & 0.9, 1-H), 6.18 (1, dd, J, 10.1 & 0.5, 7-H), 4.70 (2, m, 5-H & 14-OH), 3.84 (3, s, 3-OCH$_3$), 3.35 (1, d, J, 6.1, 9-H), 3.14 (1, d, J, 18.6, 10-H$_\beta$), 2.75 (1, ddd, J, 13.7, 4.3 & 1.4, 16-H$_e$), 2.55 (1, dd, J, 19.4 & 6.0, 10-H$_\alpha$), 2.45 (2, d, J, 6.6, —N—CH$_2$-cyclopropyl), 2.38 (1, td, J, 13.8 & 4.3, 16-H$_a$), 2.26 (1, td, J, 12.1 & 3.7, 15-H$_a$), 1.70 (1, dd, J, 13.9 & 2.7, 15-H$_e$), 0.97–0.80 (1, m, N—CH$_2$—CH in cyclopropyl ring), 0.58 (2, AB, CH—CH in cyclopropyl ring) and 0.17 (2, AB, CH—CH in cyclopropyl ring).

EXAMPLE 39

Preparation of 17-cyclopropylmethyl-14-hydroxynorcodeinone (5-7) from 17-cylororopylmethyinorcodeinone dienol acetate (5-6) by MCPBA A solution of 17-cyclopropylmethylnorcodeinone dienol acetate (0.5 g, 1.31 mmol), 3-chloroperbenzoic acid (0.36 g, 2.10 mmol) and oxalic acid (0.27 g,2.90 mmol) in acetic acid (7 ml) was stirred at rt. overnight, added cold water (35 ml), basified with sodium carbonate, and extracted with methylene chloride (100 ml). The extract was washed with water (2×30 ml), dried over anhydrous sodium sulfate, and evaporated in vacuo to dryness. The residue (0.41 g) was chromatographed on silica gel to give 17-cyclopropylmethyl-14-hydroxynorcodeinone (0.34 g, 74% yield). The $R_f$ value in TLC and the IR spectrum of the product were comparable to those obtained from an authentic sample.

EXAMPLE 40

Preparation of 3-methylnaltrexone (5-8)

A mixture of 17-cyclopropylmethyl-14-hydroxynorcodeinone (0.30 g, 0.85 mmol) and Pd/C (5%, 0.45 g) in ethanol (35 ml) was hydrogenated in a Parr hydrogenator at rt. under 28 psi of hydrogen gas. The mixture was filtered. The filtrate was evaporated in vacuo to dryness to give 3-methylnaltrexone (0.30 g, 99% yield). IR (KBr)(v, cm$^{-1}$): 1720 (st, sharp, C=O), 3380–3340 (broad, 14-OH); NMR ($\delta_H$)(CDCl$_3$): 6.70 (1, d, J, 8.2, 2-H), 6.60 (1, d, J, 8.1, 1-H), 4.65 (1,s, 5-H), 3.91 (3, s, 3-OCH$_3$), 3.17 (1, d, J, 6.0, 9-H), 3.06 (1, d, J, 18.2, 10-H$_\beta$), 3.03 (1, td, J, 14.4 & 5.2, 7-H$_a$), 2.70 (1, dd, J, 11.7 & 4.5, 16-H$_e$), 2.58 (1, dd, J, 18.4 & 6.0, 10-H$_\alpha$), 2.41 (2, d, J, 6.6, —N—C$_2$-cyclopropyl), 2.41 (2, overlap, 14-OH & 16-H$_a$), 2.29 (1, dt, J, 14.5 & 3.1, 7-H$_e$), 2.12 (1, td, J, 11.9 & 3.5, 15-H$_a$), 1.88 (1, ddd, J, 13.3, 5.2 & 3.1, 8-H$_e$), 1.67 (1, dd, J, 14.5 & 3.4, 8-H$_a$), 1.58 (1, dt, J, 12.8 & 5.1, 15-H$_e$), 0.91–0.81 (1, m, —N—CH$_2$—CH in cyclopropyl ring), 0.56 (2, AB, CH—CH in cyclopropyl ring) and 0.15 (2, AB, CH—CH in cyclopropyl ring).

EXAMPLE 41

Preparation of naltrexone from 3-methylnaltrexone (5-9)

A solution of 3-methylnaltrexone (0.48 g, 1.35 mmol) in methylene chloride (30 ml) was cooled with an ice-water bath, and then added a solution of boron tribromide (5.4 ml, 1M solution in methylene chloride, 5.4 mmol). The reaction mixture was stirred at rt. for 15 hr, basified with NH$_4$OH, and extracted with methylene chloride (60 ml). The extract was washed with water (2×15 ml), dried over anhydrous sodium sulfate, and evaporated in vacuo to dryness to give naltrexone (0.45 g, 98% yield). IR (KBr)(v, cm$^{-1}$): 1725 (st, sharp, C=O), 3620–3040 (broad, 3-OH & 14-OH); NMR ($\delta_H$)(CDCl$_3$): 6.72 (1, d, J, 8.2, 2-H), 6.57 (1, d, J, 8.2, 1-H), 5.18 (2, s (broad), 3-OH & 14-OH), 4.69 (1,s, 5-H), 3.18 (1, d, J, 5.8, 9-H), 3.05 (1, d, J, 18.5, 10-H$_\beta$), 3.05 (1, td, J, 14.3 & 5.3, 7-H$_a$), 2.71 (1, dd, J, 11.4 & 4.3, 16-H$_e$), 2.56 (1, dd, J, 18.8 & 5.9, 10-H$_\alpha$), 2.41 (2, d, J, 6.6, —N—CH$_2$-cyclopropyl), 2.41 (1, overlap, 16-H$_a$), 2.30 (1, dt, J, 14.7 & 3.1, 7-H$_e$), 2.18 (1, td, J, 12.1 & 3.7, 15-H$_a$), 1.90 (1, dd, J, 13.3 & 4.0, 8-H$_e$), 1.63 (1, dd, J, 14.4 & 3.2, 8-H$_a$), 1.57 (1, dm, J, 9.9, 15-H$_e$), 0.91–0.81 (1, m, N—CH$_2$—CH in cyclopropyl ring), 0.55 (2, AB, AB, CH—CH in cyclopropyl ring) and 0.15 (2, AB, CH—CH in cyclopropyl ring).

F. Synthesis of Naltrexone From Morphine Through 3-Benzyl-17-Cyclopropylmethylnormorphinone 6-1 (see 3-1 & 4-1)

6-2 (see 4-2)

EXAMPLE 42

Preparation of 3-benzyl-17-cyclopropylmethylnormornhine (6-4) from 6-acetyl-3-benzylmorphine (6-2)

A solution of 6-acetyl-3-benzylmorphine (13.17 g, 31.5 mmol), 1,8-bis-(dimethylamino)naphthalene (proton sponge, 1.34 g, 6.25 mmol), and 1-chloroethyl chloroformate (ACE-Cl, 7.03 g, 98% pure, 48.2 mmol) in ClCH$_2$CH$_2$Cl was heated at reflux for 1.5 hrs. To this reaction mixture, was added MeOH (100 ml) and conc. HCl (8 drops). The reflux was continued for another 3 hr. The mixture was cooled and evaporated to dryness in vacuo to give 3-benzylnormorphine hydrochloride as white flakes (15.05 9). IR (KBr)(v, cm$^{-1}$): 3550 (m, sharp), 3400 (m, b), 2475 (s, sharp); NMR ($\delta_H$)(DMSO-d$_6$): 10.35–9.62 (2 b, $^+$NH$_2$Cl$^-$), 7.49–7.21 (5, m, —C$_6$H$_5$), 6.74 (1, d, J, 8.2, 2-H), 6.54(1, d, J, 8.2, 1-H), 5.77(1, dm, J, 9.8, 7-H), 5.23(1, dm, J, 10.2, 8-H), 5.13 (2, AB, OCH$_2$Ph), 4.89 (1, dd, J, 6.4 & 1.1, 5-H), 4.41 (d, J, 6.6, 9-H), 4.28–4.09 (2, m, 6-H & OH), 3.4–2.8 (2, m, 10-H$_\beta$ & 10-H$_\alpha$), 3.4–2.8 (1, m, 14-H), 3.4–2.8 (2, m, 16-H$_a$ & 16-H$_e$), 2.39 (1, td, J, 13.3 & 5.1, 15-H$_a$), 2.02 (1, dm, J, 10.6, 15-H$_e$).

A suspension of 3-benzylnormorphine (31.5 mmol, crude), chloromethylcyclopropane (5.81 g, 64.2 mmol), and Na$_2$CO$_3$ (20.54 g, 194 mmol) in 2-propanol (150 ml) was heated at reflux for a day. The solvent was evaporated off in vacuo. The residue was added water and extracted with CH$_2$Cl$_2$ (250 ml). The extract was dried over anhydrous Na$_2$SO$_4$ and evaporated in vacuo to dryness to give a crude product (16.08 g), which was chromatographed on silica gel (column: d=6 cm, l=13.5 cm; eluting solvent: 4% MeOH in CH$_2$Cl$_2$) to give 3-benzyl-17-cyclopropylmethylnormorphine (13 g, 100%). IR (KBr)(v, cm$^{-1}$): 3440 (m, b, —OH); NMR ($\delta_H$)(CDCl$_3$): 7.56–7.10 (5, m, —C$_6$H$_5$), 6.69 (1, d, J, 8.1, 2-H), 6.48 (1, d, J, 8.2, 1-H), 5.64 (1, dm, J, 9.9, 7-H), 5.28 (1, dm, J, 9.8, 8-H), 5.11 (2, AB, OCH$_2$Ph), 4.85 (1, dd, J, 6.5 & 1.3, 5-H), 4.23–4.02 (1, m, 6-H), 3.64 (1, dd, J, 6.4 & 3.2, 9-H), 2.91 (1, d, J, 18.4, 10-H$_\beta$), 2.73 (1, dm, J, 11.8, 16-H$_e$), 2.72–2.55 (1, m, 14-H), 2.72–2.55 (1, m, —OH), 2.48–2.20 (1, m, 16-H$_a$), 2.42 (2, d, J, 6.4, N—CH$_2$-cyclopropyl), 2.27 (1, dd, J, 18.6 & 6.2, 10-H$_\alpha$), 2.07 (1, td, J, 12.2 & 5.1, 15-H$_a$), 1.84 (1, dm, J, 13.0, 15-H$_e$), 1.0–0.7 (1, m, m, N—CH$_2$—CH in cyclopropyl ring), 0.53 (2, AB, CH—CH in cyclopropyl ring), 0.14 (2, AB, CH—CH in cyclopropyl ring).

EXAMPLE 43

Preparation of 3-benzyl-17-cyclopropylmethylnormorphinone (6-5)

To a solution of DMSO (5.88 g, 75.3 mmol) in CH$_2$Cl$_2$ (80 ml) at −78° C. was added a solution of oxalyl chloride (4.51 g, 35.5 mmol) in CH$_2$Cl$_2$ (10 ml) in 10 min. This solution was allowed to stir at −78° C. for 20 min. then was added a solution of 3-benzyl-17-cyclopropylmethylnormorphine (7.06 g, 17.0 mmol) in CH$_2$Cl$_2$ (30 ml) in 30 min. The resulting solution was allowed to stir at −78° C. for 3 hr. Et$_3$N (20 ml, 148 mmol) was added. The mixture was allowed to warm up to rt., washed with water (5×80 ml), dried over anhydrous Na$_2$SO$_4$, and evaporated in vacuo to dryness to give a reddish oil (7.98 g), which was chromatographed on silica gel (column: d=5 cm, l=19 cm; eluting solvent: 5% MeOH in EtOAc) to give 3-benzyl-17-cyclopropylmethylnormorphinone (5.56 g, 79% yield). IR (KBr)(v, cm$^{-1}$): 1670 (s, sharp, C=C—C=O); NMR ($\delta_H$)(CDCl$_3$): 7.52–7.18 (5, m, —C$_6$H$_5$), 6.69 (1, d, J, 8.2, 2-H), 6.64 (1, dd, J, 10.5 & 2.2, 8-H), 6.52 (1, d, J, 8.2, 1-H), 6.07 (1, dd, J, 10.2 & 3.1, 7-H), 5.17 (2, s, OCH$_2$Ph), 4.70 (1, s, 5-H), 3.68 (1, dd, J, 5.4 & 2.9, 9-H), 3.29–3.16 (1, m, 14-H), 2.98 (1, d, J, 18.3, 10-H$_\beta$), 2.83 (1, dm, J, 10.7, 16-H$_e$), 2.6–2.3 (1, m, 10-H$_\alpha$), 2.41 (2, AB, N—CH$_2$-cyclopropyl), 2.24 (1, td, J, 11.7 & 3.2, 16-H$_a$), 2.07 (1, td, J, 11.6 & 4.8, 15-H$_a$), 1.84 (1, dm, J, 13.0, 15-H$_e$), 1.0–0.78 (1, m, N—CH$_2$—CH in cyclopropyl ring), 0.55 (2, AB, CH—CH in cyclopropyl ring), 0.15 (2, AB, CH—CH in cyclopropyl ring); MS (El), m/e (%): 413 (M$^+$, 8), 322 (28, [M—CH$_2$Ph]$^+$), 91 (68, [CH$_2$Ph]$^+$), 55 (100, [CH$_2$C$_3$H$_5$]$^+$).

EXAMPLE 44
Preparation of 3-benzyl-17-cyclopropylmethylnormorphinone dienol acetate (6-6)

A mixture of 3-benzyl-17-cyclopropylmethyinormorphinone (4.34 g, 10.5 mmol), NaOAc (1.92 g, 23.4 mmol), Ac$_2$O (44.14 g, 432.4 mmol) in toluene (10 ml) was heated at 100° C. for 20 hr., cooled, basified with aqueous NaHCO$_3$, and extracted with CH$_2$Cl$_2$ (300 ml). The extract was washed with water (3×150 ml), dried over anhydrous Na$_2$SO$_4$, and evaporated in vacuo to dryness to give an oil (5.57 g), which was chromatographed on silica gel (column: d=5 cm, l=19.5 cm; eluting solvent: EtOAc) to obtain 3-benzyl-17-cyclopropylmethylnormorphinone dienol acetate (3.0 g, 63% yield). IR (KBr)(v, cm$^{-1}$): 1760 (s, sharp, C=C—C=C—OAc); NMR ($\delta_H$)(CDCl$_3$): 7.51–7.20 (5, m, C$_6$H$_5$), 6.68 (1, d, J, 8.1, 2-H), 6.52 (1, d, J, 8.3, 1-H), 5.77 (1, dd, J, 6.3 & 0.9, 7-H), 5.55 (1, d, J, 6.3, 8-H), 5.48 (1, s, 5-H), 5.14 (2, s, OCH$_2$Ph), 3.92 (1, d, J, 7.0, 9-H), 3.25 (1, d, J, 17.9, 10-H$_\beta$), 2.95–2.80 (2, m, 16-H$_a$ & 16-H$_e$), 2.74 (1, dd, J, 18.5 & 7.3, 10-H$_\alpha$), 2.49 (2, s, N—CH$_2$-cyclopropyl ), 2.29 (1, td, J, 12.4 & 6.5, 15-H$_a$), 2.19 (3, s, m, C=C—C=C—OAc), 1.72 (1, dm, J, 12.4,15-H$_e$), 1.0–0.8 (1, m, CH$_2$—CH in cyclopropyl ring), 0.55 (2, AB, CH—CH in cyclopropyl ring), 0.15 (2, AB, CH—CH in cyclopropyl ring); MS (El), m/e (%): 455 (M$^+$, 16), 364 (27, [M—CH$_2$Ph]$^+$), 322 (28, [M—CH$_2$Ph—CH$_2$=C=C)]$^+$), 91 (68, [CH$_2$Ph]$^+$), 55 (100, [CH$_2$C$_3$H$_5$]$^+$).

EXAMPLE 45
Preparation of 3-benzyl-17-cyclopropylmethyl-14-hydroxynormorphinone (6-7) from 3-benzyl-17-cyclopropylmethyl-14-hydroxynormorphinone dienol acetate (6-6) by MCPBA A solution of 3-benzyl-17-cyclopropylmethylnormorphinone dienol acetate (0.61 g, 1.34 mmol), oxalic acid (0.25 g, 2.8 mmol), and 3-chloroperbenzoic acid (0.36 g, 57–86%, 1.2–1.8 mmol) in AcOH (5.44 g, 88.9 mmol) was stirred at rt. for 5 hr, basified with cold aqueous NaHCO$_3$, extracted with CH$_2$Cl$_2$ (120 ml). The extract was dried over anhydrous Na$_2$SO$_4$ and evaporated in vacuo to dryness to give an oily residue (0.93 g), which was chromatographed on silica gel (column: d=2.54 cm, l=23 cm; eluting solvent: 1% MeOH in CH$_2$Cl$_2$) to obtain 3-benzyl-17-cyclopropylmethyl-14-hydroxynormorphinone (0.46 g, 80% yield). The R$_f$ value in TLC and the IR spectrum of the product were comparable to those obtained from an authentic sample.

EXAMPLE 46
Preparation of 3-benzyl-17-cyclopropylmethyl-14-hydroxynormorphinone (6-7) from 3-benzyl-17-cyclopropylmethyl-14-hydroxymorphinone dienol acetate (6-6) by H$_2$O$_2$ in HCOOH A solution of 3-benzyl-17-cyclopropylmethylnormorphinone dienol acetate (0.91 g, 2.0 mmol), formic acid (6.02 g, 90%, 117.7 mmol), and H$_2$O$_2$ (0.28 g, 30%, 2.47 mmol) was heated at 35–46° C. for 3 hr., basified with cold aqueous NaHCO$_3$, extracted with CH$_2$Cl$_2$ (200 ml). The extract was washed with water (50 ml), dried over anhydrous Na$_2$SO$_4$ and evaporated in vacuo to dryness to give an oily residue (1.15 g), which was chromatographed on silica gel (column: d=2.54 cm, l=19 cm; eluting solvent: 3% MeOH in CH$_2$Cl$_2$) to obtain 3-benzyl-17-cyclopropylmethyl-14-hydroxynormorphinone (0.75 g, 87% yield). IR (KBr)(v, cm$^{-1}$): 3300 (m, OH), 1680 (s, sharp, C=C—C=O); NMR ($\delta_H$)(CDCl$_3$): 7.43–7.19 (5, m. C$_6$H$_5$), 6.71 (1, d, J, 8.1, 2-H), 6.62 (1, d, J, 9.8, 8-H), 6.53 (1, d, J, 8.2, 1-H), 6.18 (1, d, J, 10.1, 7-H), 5.16 (2, s, OCH$_2$Ph), 4.73 (1, s, 5H), 3.34 (1, d, J, 6.1, 9-H), 3.12 (1, d, J, 18.6, 10-H$_\beta$), 2.74 (1, dm, J, 11.1, 16-H$_e$), 2.53 (1, dd, J, 19.2 & 6.0, 10-H$_\alpha$), 2.55–2.35 (1, b, —OH), 2.55–2.35 (1, m, 15-H$_a$), 2.44 (2, d, J, 6.4, N—CH$_2$-cyclopropyl), 2.25 (1, td, J, 11.8 & 3.4, 16-H$_a$), 1.69 (1, dm, J, 13.0, 15-H$_e$), 0.98–0.78 (1, m, CH$_2$—CH in cyclopropyl ring), 0.58 (2, AB, CH—CH in cyclopropyl ring), 0.16 (2, AB, CH—CH in cyclopropyl ring); MS (El), m/e (%): 429 (M$^+$, 32), 338 (75, [M—CH$_2$Ph]$^+$), 91 (100, [CH$_2$Ph]+), 55 (97, [CH$_2$C$_3$H$_5$]$^+$).

EXAMPLE 47
Preiparation of naltrexone (6-8) from 3-benzyl-17-cyclopropylmnethyl-14-hydroxynormorphinone (6-7)

A mixture of 3-benzyl-17-cyclopropylmethyl-14-hydroxynormorphinone (0.40 g, 0.93 mmol) and 5% Pd/C (0.25 g) in 2-propanol (60 ml) was hydrogenated under 30 psi at rt. overnight, filtered through celite, and evaporated to dryness to give naltrexone (0.32 g, 100% yield). The R$_f$ value in TLC and the IR spectrum of the product were comparable to those obtained from an authentic sample.

Although the invention has been illustrated by the preceding examples, they are not to be construed as being limited to the materials employed therein, but rather the invention is directed to the generic as hereinbefore disclosed. Various modifications and embodiments can be made without departing from the spirit or scope thereof.

What is claimed is:

1. A process of preparing oxymorphone from morphine, comprising:

(1) reacting morphine with (a) an acyl halide or anhydride having the formula R"C(O)-X and [R"C(O)]$_2$O, respectively, wherein R" is lower alkyl group and X is halogen, to form 3-acylmorphine;

(2) oxidizing the hydroxy group of the 3-acylmorphine with an oxidizing agent so as to form the corresponding 3-acylmorphinone;

(3) and either by (3a) or (3b):

(3a) introducing a β-oriented hydroxy group at the 14-position of the 3-acylmorphinone with aqueous hydrogen peroxide and an acid at a temperature of about 15° to about 70° C. to form the 3-acyl-14-hydroxymorphinone;

(3b) acylating the 3-acylmorphinone with an acylating agent so as to form 3-acylmorphinone dienol acylate followed by oxidizing the dienol acetate to the corresponding 3-acyl-14-hydroxymorphinone;

(4) hydrogenating the 3-acyl-14-hydroxymorphinone with a catalyst so as to form the 3-acyloxymorphone;

(5) hydrolyzing the acyloxymorphone with aqueous acidic or basic solution to form oxymorphone.

2. A process of preparing oxymorphone from morphine, comprising:

(1) reacting morphine with benzyl halide so as to form 3-benzylmorphine;

(2) oxidizing the hydroxy group of the 3-benzylmorphine with an oxidizing agent so as to form the corresponding 3-benzylmorphinone;

(3) and either by (3a) or (3b):

(3a) introducing a β-oriented hydroxy group at the 14-position of the 3-benzylmorphinone with aqueous hydrogen peroxide and an acid at a temperature of about 15° to about 70° C. so as to form the 3-benzyl-14-hydroxymorphinone; or (3b) acylating the 3-benzylmorphinone with an acylating agent so as to form 3-benzylmorphinone dienol acylate followed by oxidizing the dienol acetate to the corresponding 3-benzyl-14-hydroxymorphinone;

(4) hydrogenating the 3-benzyl-14-hydroxymorphinone with a catalyst so as to form oxymorphone.

* * * * *

UNITED STATES PATENT AND TRADEMARK OFFICE
CERTIFICATE OF CORRECTION

PATENT NO. : 5,922,876
DATED : July 13, 1999
INVENTOR(S) : Bao-Shan Huang et al.

Page 1 of 2

It is certified that error appears in the above-identified patent and that said Letters Patent is hereby corrected as shown below:

Column 2,
Line 43, the formula:                should read:

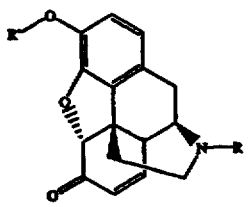

All that portion at column 2, lines 14 through 55, and the portion of line 56 reading "of an acid such as formic" should appear at column 3 just before line 33, which begins "acid, tartaric"

Column 9,
Line 53, "$R_2$" should read -- $P_2$ --

Column 10,
Line 44, "unhydrite" should read -- anhydride --

Column 25,
Lines 46 and 62, at each occurrence "(3-3)" should read: -- (2-3) --

Column 28,
Line 37, "D." should appear before -- Synthesis --

Column 29,
Line 25, "(4-2)" should appear after -- 6-acetyl-3-benzylmorphine --

Column 32,
Line 1, "E." should appear before -- Synthesis --

UNITED STATES PATENT AND TRADEMARK OFFICE
CERTIFICATE OF CORRECTION

PATENT NO. : 5,922,876
DATED : July 13, 1999
INVENTOR(S) : Bao-Shan Huang et al.

It is certified that error appears in the above-identified patent and that said Letters Patent is hereby corrected as shown below:

Claim 1,
Line 3, "with (a) an" should read -- with an --

Signed and Sealed this

Twenty-seventh Day of November, 2001

*Attest:*

NICHOLAS P. GODICI
*Attesting Officer*    *Acting Director of the United States Patent and Trademark Office*